US008697059B2

(12) United States Patent
Van Epps et al.

(10) Patent No.: US 8,697,059 B2
(45) Date of Patent: Apr. 15, 2014

(54) COMPOSITIONS AND SOFT TISSUE REPLACEMENT METHODS

(71) Applicant: Allergan, Inc., Irvine, CA (US)

(72) Inventors: Dennis Van Epps, Goleta, CA (US); Guang-Liang Jiang, Irvine, CA (US); Wha Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/886,965

(22) Filed: May 3, 2013

(65) Prior Publication Data
US 2013/0243740 A1    Sep. 19, 2013

Related U.S. Application Data

(63) Continuation of application No. 13/532,036, filed on Jun. 25, 2012, now Pat. No. 8,518,396, which is a continuation of application No. 13/193,744, filed on Jul. 29, 2011.

(60) Provisional application No. 61/375,144, filed on Aug. 19, 2010.

(51) Int. Cl.
*A01N 63/00*    (2006.01)
*A61K 35/32*    (2006.01)
*A01N 35/00*    (2006.01)

(52) U.S. Cl.
USPC .............. 424/93.7; 424/574; 514/573; 623/8; 623/9; 623/10

(58) Field of Classification Search
USPC .................. 424/97.3, 574; 623/8, 9, 10, 11.1; 514/573
See application file for complete search history.

(56) References Cited

U.S. PATENT DOCUMENTS

| | | | |
|---|---|---|---|
| 5,972,385 A | 10/1999 | Liu et al. | |
| 6,129,761 A | 10/2000 | Hubbell | |
| 6,875,787 B2 * | 4/2005 | Donde | 514/385 |
| 6,991,652 B2 | 1/2006 | Burg | |
| 7,129,209 B2 | 10/2006 | Rhee | |
| 7,316,822 B2 | 1/2008 | Binette | |
| 7,767,452 B2 | 8/2010 | Kleinsek | |
| 7,799,767 B2 | 9/2010 | Lamberti et al. | |
| 7,875,296 B2 | 1/2011 | Binette | |
| 8,053,423 B2 | 11/2011 | Lamberti et al. | |
| 8,137,702 B2 | 3/2012 | Binette et al. | |
| 8,153,591 B2 | 4/2012 | Masters et al. | |
| 8,246,947 B2 | 8/2012 | Hedrick et al. | |
| 8,288,347 B2 | 10/2012 | Collette et al. | |
| 8,420,077 B2 | 4/2013 | Altman et al. | |
| 8,480,735 B2 | 7/2013 | Rigotti et al. | |
| 8,496,702 B2 | 7/2013 | Rigotti et al. | |
| 8,518,396 B2 | 8/2013 | Van Epps et al. | |
| 2005/0025755 A1 | 2/2005 | Hedrick et al. | |
| 2005/0181007 A1 * | 8/2005 | Hunter et al. | 424/423 |
| 2006/0029578 A1 | 2/2006 | Hoemann et al. | |
| 2007/0104692 A1 | 5/2007 | Quijano et al. | |
| 2007/0104693 A1 | 5/2007 | Quijano et al. | |
| 2007/0196421 A1 * | 8/2007 | Hunter et al. | 424/423 |
| 2009/0098177 A1 | 4/2009 | Werkmeister et al. | |
| 2009/0123547 A1 | 5/2009 | Hill et al. | |
| 2009/0124552 A1 | 5/2009 | Hill et al. | |
| 2009/0162415 A1 | 6/2009 | Huang et al. | |
| 2009/0181104 A1 | 7/2009 | Rigotti et al. | |
| 2009/0317376 A1 | 12/2009 | Zukowska et al. | |
| 2010/0168780 A1 | 7/2010 | Rigotti et al. | |
| 2010/0249924 A1 | 9/2010 | Powell et al. | |
| 2011/0008436 A1 | 1/2011 | Altman et al. | |
| 2011/0008437 A1 | 1/2011 | Altman et al. | |
| 2011/0014287 A1 | 1/2011 | Altman et al. | |
| 2011/0052695 A1 | 3/2011 | Jiang et al. | |
| 2011/0070281 A1 | 3/2011 | Altman | |
| 2011/0097381 A1 | 4/2011 | Binette | |
| 2011/0104800 A1 | 5/2011 | Kensy et al. | |
| 2011/0150823 A1 | 6/2011 | Huang | |
| 2011/0150846 A1 | 6/2011 | Van Epps | |
| 2011/0183001 A1 | 7/2011 | Rosson et al. | |
| 2011/0183406 A1 | 7/2011 | Kensy | |
| 2011/0194945 A1 | 8/2011 | Kensy et al. | |
| 2011/0295238 A1 | 12/2011 | Kensy et al. | |
| 2012/0010146 A1 | 1/2012 | Han et al. | |
| 2012/0045420 A1 | 2/2012 | Van Epps et al. | |
| 2012/0076868 A1 | 3/2012 | Lamberti et al. | |
| 2012/0100611 A1 | 4/2012 | Kensy et al. | |
| 2012/0136011 A1 * | 5/2012 | Jiang et al. | 514/260.1 |
| 2012/0156265 A1 | 6/2012 | Binette et al. | |

(Continued)

FOREIGN PATENT DOCUMENTS

| | | |
|---|---|---|
| WO | WO 2006098918 A2 * | 9/2006 |
| WO | 2008148071 | 12/2008 |
| WO | 2009003135 | 12/2008 |
| WO | 2011072399 | 6/2011 |

OTHER PUBLICATIONS

Sakai et al. Kobe J. Med. Sci. (2001) 47: 35-35.*
Altman et al., "Adhesion, migration and mechanics of human adipose-tissue-derived stem cells on silk fibroin chitosan matrix", Acta Biomaterialia 6 (2010) 1388-1397.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.

(Continued)

*Primary Examiner* — Susan Hanley
(74) *Attorney, Agent, or Firm* — Linda Fox; Stephen Donovan

(57) ABSTRACT

The present specification discloses compositions and methods for use in breast augmentation procedures. The compositions include adipose tissue and compounds that upregulate both FGF-2 and VEGF, promote new blood vessel formation thereby reducing tissue volume loss and increasing survival rate of the adipose tissue when the composition is introduced into breast tissue.

8 Claims, 7 Drawing Sheets

(56) References Cited

U.S. PATENT DOCUMENTS

| | | |
|---|---|---|
| 2012/0164116 A1 | 6/2012 | Van Epps |
| 2012/0165935 A1 | 6/2012 | Van Epps |
| 2012/0172317 A1 | 7/2012 | Altman et al. |
| 2012/0172985 A1 | 7/2012 | Altman et al. |
| 2012/0207837 A1 | 8/2012 | Powell et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0265297 A1 | 10/2012 | Altman et al. |
| 2012/0269777 A1 | 10/2012 | Van Epps et al. |
| 2013/0116188 A1 | 5/2013 | Pollock et al. |
| 2013/0116411 A1 | 5/2013 | Pollock et al. |
| 2013/0129835 A1 | 5/2013 | Pollock et al. |
| 2013/0131655 A1 | 5/2013 | Rigotti et al. |
| 2013/0244943 A1 | 9/2013 | Yu et al. |

OTHER PUBLICATIONS

Taguchi et al., "An improved method to prepare hyaluronic acid and type II collagen composite matrices", Journal of Biomedical Materials Research (2002), 61(2), 330-336.

Greco et al., "Hyaluronic Acid Stimulates Human Fibroblast Proliferation Within a Collagen Matrix", J. Cell. Physiol. 177 (3):465-473, 1998.

Calderon et al., "Type II Collagen-Hyaluronan Hydrogel—A Step Towards a Scaffold for Intervertebral Disc Tissue Engineering", European Cells and Materials, vol. 20, pp. 134-148, 2010.

Doillon et al., "Fibroblast growth on a porous collagen sponge containing hyaluronic acid and fibronectin", Biomaterials 8 (1087) 195-200.

Davidenko et al., "Xollagen-hyaluronic acid scaffolds for adipose tissue engineering", Acta Biomaterialia 6 (2010) 3957-3968.

\* cited by examiner (a) KOH, I-$R^2$, dioxane/$H_2O$;  (b) KOH, I-$R^3$, dioxane/$H_2O$;  (c) KOH, 1,2-dibromoethane, dioxane/$H_2O$;  (d) KOH, dioxane/$H_2O$.

(a) KOH, MeI, dioxane/$H_2O$; (b) Baker's Yeast, D-glucose, $H_2O$; (c) TBSOTf, 2,6-lutidine, $CH_2Cl_2$; (d) LDA, THF; PhSeCl; (e) 30% $H_2O_2$, $CH_2Cl_2$.

(a) TBSCl, etc.; (b) n-BuLi; $(CH_2O)_n$ = paraformaldehyde; (c) $Ac_2O$, pyridine; (d) Jones oxidation; (e) MeOH, AcCl; (f) $PPh_3$, $I_2$, imidazole, $CH_2Cl_2$.

(a) Cp$_2$ZrHCl, NIS; (b) t-BuLi, THF -78 °C; (c) Me$_2$Zn; (d) HF-pyridine, CH$_3$CN; separate diastereomers; (e) rabbit liver esterase, pH 7.2 phosphate buffer, CH$_3$CN; (f) NiCl$_2$, NaBH$_4$, ethylenediamine, H$_2$, THF.

(a) n-BuLi; ethylene oxide; (b) Dess-Martin [O]; (c) ethynylmagnesium bromide; (d) TBSCl, DMAP, Et₃N; (e) Cp₂ZrHCl; NIS.

(a) ClCO$_2$CH$_2$CH$_3$, Et$_3$N, CH$_2$Cl$_2$; NH$_4$OH $_{(aq)}$;
(b) EDCI, N-hydroxysuccinimide, H$_2$NCH$_2$CH$_2$OH, DMF.

COMPOSITIONS AND SOFT TISSUE REPLACEMENT METHODS

This application is a continuation of U.S. patent application Ser. No. 13/532,036, filed on Jun. 25, 2012, which is a continuation of U.S. patent application Ser. No. 13/193,744, filed on Jul. 29, 2011, which claims priority to and the benefit of U.S. Provisional Patent Application No. 61/375,144, filed on Aug. 19, 2010, the entire disclosure of each of these applications being incorporated herein by this specific reference.

Soft tissue replacement methods are commonly used for a wide variety of clinical and cosmetic purposes. One use involves reconstructive applications that rebuild and restore a body part or structure to correct deformities from congenital anomalies, trauma, cancer, infections, disease, or medication side effects. The replacement tissue serves to support surrounding tissue and to maintain the normal appearance of the body. The restoration of this normal appearance has an extremely beneficial psychological effect on post-operative patients, alleviating much of the shock and depression that often follows extensive surgical procedures. Another use involves augmentation applications that alter a body part or structure usually to improve its cosmetic or aesthetic appearance. Augmentation of the appearance also has beneficial psychological effects that improve self-esteem, well-being, and confidence of an individual. A third use involves structural applications that provides support to a body part or structure to improve its function, thereby alleviating a symptom associated with a disorder involving soft tissue loss. Examples of such disorders include, without limitation, stress urinary incontinence, fecal incontinence, vocal cord paralysis, vocal atrophy, vocal implantation, intubation trauma, post-hemilaryngectomy defects, irradiation damage, lumbar disc repair, and plantar footpad repair.

Soft tissue replacement methods currently rely on two general approaches: 1) implantation of artificial or alloplastic fillers like soft tissue implants, and injectable polymers and hydrogels; and 2) transplantation of tissue like tissue flaps and autologous tissue transfers. A drawback to the use of artificial or alloplastic fillers it that these inorganic materials lack any metabolic activity, do not become physiologically incorporated into the body, and as such, surrounding tissue and blood supply does not develop within the implanted material. In addition, artificial or alloplastic fillers risk migration and/or extrusion from the implant site. Furthermore, many of these fillers produce only temporary effects because the body rapidly reabsorbs them. Fillers providing long-term effects frequently induce a foreign body response resulting in formation of an avascular, fibrous capsule around the filler, which limits performance, distorts the aesthetic appearance of the surrounding area, and can cause pain to the individual. Furthermore, long-term fillers, like soft tissue implants, do not remodel with the aging tissue resulting in a material that may not be aesthetically acceptable as the patient's tissues undergo the normal physiologic changes associated with aging.

Although the use of transplanted tissue avoids the problems associated with artificial or alloplastic fillers, drawbacks are also associated with these procedures. In these procedures, loss of transplanted tissue volume over time as a result of its resorption by the body is a major problem. For example, transplantation of adipose tissue generally results in a loss of 20% to 90% of it volume one year after. This tissue loss is unpredictable and is a result of poor survival of the transplanted tissue due to necrosis and a lack of vascular formation. With respect to adipose tissue, tissue breakdown is associated with traumatic rupture of the cells, avascular necrosis, apoptosis of the adipocytes, inflammation secondary to apoptosis, fibrosis and contraction of the graft, and/or delipidation of the adipocytes with subsequent volume loss. Failed tissue grafts sometime produce stellate and irregular nodules with calcifications. As such, transplanted tissue methods are usually performed two or three times to obtain the desired effect, resulting in massive time and cost.

One of the major underlying causes for tissue breakdown seen in transplanted tissue methods is the lack of a blood supply sufficient to support the transplanted tissue. For example, alleviation of tissue ischemia is critically dependent upon formation of new blood vessels. The growth of new blood vessels and associated vasculature or repair or remodeling of existing blood vessels and associated vasculature provides collateral circulation in and around an ischemic area, improves blood flow, and alleviates the symptoms caused by the ischemia. Thus, compositions and methods that promote new blood vessel formation within a transplanted tissue are needed as this will improve the survival rate of such tissues, thereby achieving reliable long-term survival of grafted tissues.

The present specification provides novel compositions and soft tissue replacement methods using such compositions that reduce tissue volume loss by increasing the survival rate of the transplanted tissue. This improved survival rate is achieved by administering a compound that promotes new blood vessel formation, thereby ensuring that a blood supply adequate to support the transplanted tissue is established.

Thus, aspects of the present specification disclose a composition comprising adipose tissue and a compound having the structure of formula I,

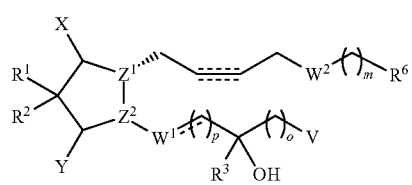

wherein each dashed line represents the presence or absence of a bond; $R^1$, $R^2$ and $R^3$ are each independently selected from H or $C_1$-$C_6$ alkyl; $R^6$ is $CO_2H$, $CO_2R^7$, $CON(R^7)_2$, $CONHCH_2CH_2OH$, $CON(CH_2CH_2OH)_2$, $CH_2OR^7$, $P(O)(OR^7)_2$, or

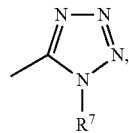

a pharmaceutically acceptable salt thereof, or a pharmaceutically acceptable amine salt thereof; $R^7$ is H, $C_1$-$C_6$ alkyl or $C_2$-$C_6$ alkenyl; X and Y are each independently selected from H, OH, =O, Cl, Br, I, or $CF_3$; $Z^1$ and $Z^2$ are each independently selected from CH or N; $W^1$ and $W^2$ are each independently selected from CH, $CH_2$, aryl or substituted aryl, heteroaryl, substituted heteroaryl; m is 0 to 6; o is 0 to 4; p is 0 or 1; and V is $C_1$-$C_6$ alkyl, aryl, substituted aryl, heteroaryl, or substituted heteroaryl.

Other aspects of the present specification disclose a method of treating a soft tissue condition of an individual, the method comprising the step of administering a composition disclosed herein to a site of the soft tissue condition, wherein administration of the composition promotes formation of a blood supply sufficient to support the transplanted tissue, thereby treating the soft tissue site. Non-limiting examples of a soft tissue condition include breast imperfection, defect, disease and/or disorder, such as, e.g., a breast augmentation, a breast reconstruction micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

Other aspects of the present specification disclose a method of treating a soft tissue condition of an individual, the method comprising the steps of a) administering the adipose tissue to a site of the soft tissue condition; and b) administering a composition comprising a compound as disclosed herein to the site of the soft tissue condition, wherein administration of the compound promotes formation of a blood supply sufficient to support the transplanted tissue, thereby treating the soft tissue site. Non-limiting examples of a soft tissue condition include those described above.

DESCRIPTION

Figure 1:
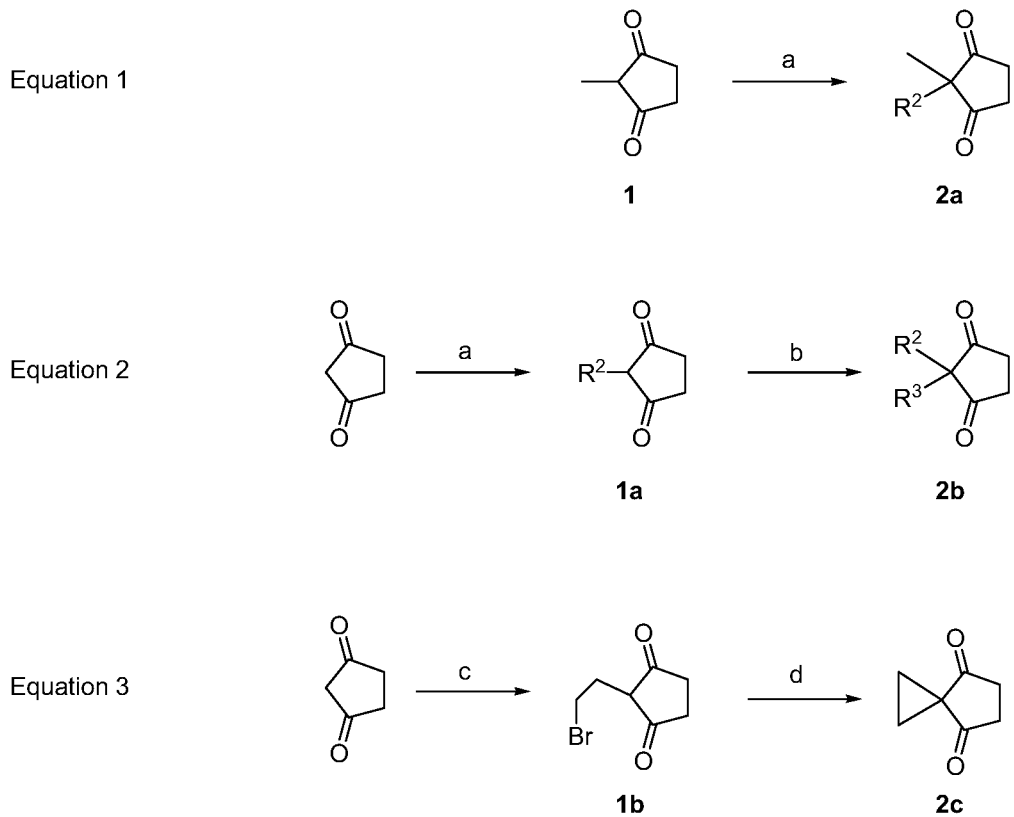
FIGS. 1-7 illustrate possible ways to prepare compounds disclosed herein.

Insufficient blood vessel formation in a repairing or otherwise metabolically active tissue results in inadequate delivery of oxygen, nutrients, and other substances necessary to establish essential physiological functions to the area and promote wound healing. The formation of blood vessels within a tissue may occur by angiogenesis and/or vasculogenesis. As used herein, the term "angiogenesis" refers to a physiological process involving the growth of new blood vessels from pre-existing vessels and includes sprouting angiogenesis, the formation of new blood vessel by sprouting off existing ones, and splitting angiogenesis (intussusception), the formation of new blood vessel by splitting off existing ones. As used herein, the term "vasculogenesis" refers to a physiological process involving the de novo production of new blood-vessels by proliferating endothelial stem cells, and as such, the formation of new blood vessels when there were no pre-existing ones.

Blood vessel formation, whether angiogenesis or vasculogenesis, requires signals form growth factors and other proteins that direct and control the process, such as, e.g., fibroblast growth factors (like FGF-1 and FGF-2), vascular endothelial growth factors (like VEGF-A and VEGF-C), angiopoietins (like Ang-1 and Ang-2), platelet derived growth factor (PDGF), monocyte chemotactic protein-1 (MCP-1) (also known as chemokine (C—C motif) ligand 2 (CCL-2)), transformation growth factor betas (TGF-β1, TGF-β2, TGF-β3, and TGF-β4), vascular cell adhesion molecules (like VCAM-1), matrix metalloproteinases (like MMP-2 and MMP-9), integrins, cadherins, plasminogen activators, plasminogen activator inhibitors, and ephrin.

Of the factors listed above, two of the more critical factors essential to new blood vessel formation are FGF-2 and VEGF. One of the most important functions of fibroblast growth factor-2 (FGF-2 or bFGF) is the promotion of endothelial cell proliferation and the physical organization of endothelial cells into tube-like structures, thus promoting angiogenesis and vasculogenesis. FGF-2 is a more potent factor in new blood vessel formation than VEGF or PDGF. As well as stimulating blood vessel growth, FGF-2 is an important factor in wound healing. This factor stimulates proliferation of fibroblasts and endothelial cells that give rise to new vessel formation and developing granulation tissue; both increase blood supply and fill up a wound space/cavity early in the wound-healing process.

VEGF is another major contributor to new blood vessel formation. VEGF is a major contributor to new blood vessel formation. VEGF causes a massive signaling cascade in endothelial cells resulting in the release of many other factors known to be responsible in new blood vessel formation. For example, binding to VEGF receptor-2 (VEGFR-2) starts a tyrosine kinase signaling cascade that stimulates the production of factors that variously stimulate vessel permeability (eNOS, producing NO), proliferation/survival (FGF-2), migration (ICAMs/VCAMs/MMPs) and finally differentiation into mature blood vessels. In addition, in vitro studies demonstrated that upon stimulation by VEGF and FGF-2, endothelial cells would proliferate, migrate, and eventually form tube structures resembling capillaries.

The compounds disclosed herein, and compositions comprising such compounds, upregulate both FGF-2 and VEGF (see Example 2). In addition, both incisional and ulcer wound models demonstrate that the upregulation of FGF-2 and VEGF results in an improved wound healing response (see Example 2).

Without wishing to be bound by any particular theory, the compounds, compositions and methods disclosed herein increase the survival rate of transplanted tissue by promoting new blood vessel formation within the transplanted tissue. Administration of a compound, either as a composition with the transplanted tissue or as a prior or subsequent administration to the transplantation procedure, upregulate factors essential to new blood vessel formation, like FGF-2 and VEGF. This upregulation initiates the signaling cascade in endothelial cells responsible for the formation of new blood vessel. This initiation results in the formation of new blood vessels that, in turn, provide oxygen, nutrients, and other substances necessary to establish essential physiological functions to the transplanted tissue. This adequate blood supply supports the establishment, growth and survival of the transplanted tissue. Thus, the compounds, compositions and methods disclosed herein ameliorate or prevent one of the major underlying causes for the tissue breakdown of transplanted tissue, namely the lack of a blood supply sufficient to support the transplanted tissue. In addition, the compounds and compositions disclosed herein are superior to the mere addition of factors critical to new blood vessel formation, like FGF-2 and VEGF, because these small molecules are more stable and less costly then these protein-based therapies. Furthermore, formation of new blood vessels can soften scar tissue, capsular contracture by facilitating the remolding of fibrous tissue into normal soft tissue typical of the affected region.

Aspects of the present specification provide, in part, a composition comprising adipose tissue. As used herein, the term "adipose tissue" is synonymous with "fat" or "fatty tissue" and refers to a loose fibrous connective tissue comprising fat cells (adipocytes) and multiple types of regenerative cells. Adipose tissue may comprise brown and/or white adipose tissue taken from anybody site, such as, e.g., subcutaneous, omental/visceral, interscapular, or mediastinal. It may be obtained from any organism having adipose tissue, or the adipose tissue used may be from a primary cell culture or an immortalized cell line.

Adipose tissue may be collected from the same individual who is undergoing the soft tissue replacement procedure (autograft), from a donor individual who is not the same individual as the one undergoing the soft tissue replacement procedure (allograft), or from an animal source (xenograft). As used herein, the term "autotransplantation" refers to the transplantation of organs, tissues, or cells from one part of the body to another part in the same individual, i.e., the donor and recipient are the same individual. Tissue transplanted by such "autologous" procedures is referred to as an autograft or autotransplant. As used herein, the term "allotransplantation" refers to the transplantation of organs, tissues, or cells from a donor to a recipient, where the donor and recipient are different individuals, but of the same species. Tissue transplanted by such "allologous" procedures is referred to as an allograft or allotransplant. As used herein, the term "xenotransplantation" refers to the transplantation of organs, tissues, or cells from a donor to a recipient, where the donor is of a different species as the recipient. Tissue transplanted by such "xenologous" procedures is referred to as a xenograft or xenotransplant.

Adipose tissue can be collected by any procedure that can harvest adipose tissue useful for the compositions and methods disclosed herein, including, without limitation a liposuction (lipoplasty) procedure or a lipectomy procedure. Procedures useful for collecting adipose tissue should minimize the trauma and manipulation associated with adipose tissue removed. Adipose tissue may be harvested from any suitable region, including, without limitation, a mammary region, an abdominal region, a thigh region, a flank region, a gluteal region, a trochanter region, or a gonadal region. Procedures useful for collecting adipose tissue are well known to a person of ordinary skill in the art. The selected procedures may be performed concomitantly with liposculpture.

A liposuction procedure harvests adipose tissue by aspirating the tissue using a cannula. The cannula may be connected to a syringe for manual aspiration or to a power assisted suction device, like an aspirator, adapted to collect the adipose tissue into a vacuum bottle. A liposuction procedure does not maintain an intact blood supply of the harvested tissue. The syringe may be a 10, 20 or 60 mL syringe fitted with a 12 or 14 gauge cannula. Non-limiting examples of liposuction procedures include suction-assisted liposuction (SAL), ultrasound-assisted liposuction (UAL), power-assisted liposuction (PAL), twin-cannula (assisted) liposuction (TCAL or TCL), or external ultrasound-assisted liposuction (XUAL or EUAL), or water-assisted liposuction (WAL). In addition, the liposuction procedures listed above can be used with any of the following procedures that vary the amount of fluid injected during the procedure, such as, e.g., dry liposuction, wet liposuction, super-wet liposuction, tumescent liposuction, or laser-assisted liposuction. An autologous soft tissue transfer procedure typically uses adipose tissue collected from a liposuction procedure.

Although the harvested tissue may be used directly to make the disclosed compositions, it is more typically processed to purify and/or enrich for healthy adipocytes and regenerative cells. For example, the harvested adipose tissue may be separated from any debris and/or contaminants such as, e.g., blood, serum, proteases, lipases, lipids and other oils, and/or other bodily fluids; tumescent fluid and/or other materials used in the liposuction procedure; and/or other impurities suctioned during the procedure. Methods useful in separating debris and/or contaminants from adipose tissue useful to make the disclosed compositions, including, without limitation, centrifugation, sedimentation, filtration, and/or absorption. In addition, or alternatively, the harvested adipose tissue may be processed by washing is a physiological buffer like saline to remove any debris and/or contaminants.

A lipectomy procedure harvests adipose tissue by surgical excision from a donor site in a manner that minimizes damage to the blood supply of the tissue using standard surgical operative procedures. This harvested tissue is then implanted into the region needing the soft tissue replacement. A tissue flap or tissue graft procedure typically uses adipose tissue collected from a lipectomy procedure. A tissue flap is a section of living tissue that maintained its blood supply as the tissue is moved from one area of the body to another.

A local flap uses a piece of skin and underlying tissue that lie adjacent to the wound, including adipose tissue. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. As an example, the transverse rectus abdominis myocutaneous flap (TRAM flap) is a tissue flap procedure that uses muscle, fat and skin from an abdomen to create a new breast mound after a mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is a patch of healthy skin that is taken from one area of the body, called the "donor site," and used to cover another area where skin is missing or damaged. There are three basic types of skin grafts. A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are needed. As its name implies, a full-thickness (all layers) section of skin from the donor site are lifted. A composite graft is used when the wound to be covered needs more underlying support, as with skin cancer on the nose. A composite graft requires lifting all the layers of skin, adipose tissue, and sometimes the underlying cartilage from the donor site.

The amount of adipose tissue collected will typically vary from individual to individual and can depend on a number of factors including, but not limited to, amount of adipose tissue required for the soft tissue replacement method, aesthetic expectations, age, body habitus, coagulation profile, hemogroup may be optionally substituted as defined herein. dynamic stability, co-morbidities, and physician preference.

A liposuction procedure may harvests form about 1 mL to about 1500 mL of adipose tissue. A lipectomy procedure typically harvests about 1 g to about 5,000 g.

Adipose tissue comprises multiple regenerative cells. As used herein, the term "regenerative cell" refers to any cells that cause or contribute to complete or partial regeneration, restoration, or substitution of structure or function of an organ, tissue, or physiologic unit or system to thereby provide a therapeutic, structural or cosmetic benefit. Examples of regenerative cells include stem cells, progenitor cells, and precursor cells. As used herein, the term "stem cell" refers to a multipotent regenerative cell with the potential to differentiate into a variety of other cell types that perform one or more specific functions and has the ability to self-renew. Some of the stem cells disclosed herein may be pluripotent. Exemplary examples of stem cells include, without limitation, adipose-derived stem cells (ASCs; adipose-derived stromal cells), endothelial-derived stem cells (ESCs), hematopoietic stem cells (HSCs), and mesenchymal stem cells (MSCs). As used herein, the term "progenitor cell" refers to an oligopotent regenerative cell with the potential to differentiate into more than one cell type, or an unipotent regenerative cell with the potential to differentiate into only a single cell type, that perform(s) one or more specific functions and has limited or no ability to self-renew. Exemplary examples of progenitor cells include, without limitation, endothelial progenitor cells, keratinocytes, monoblasts, myoblasts, and pericytes. As used herein, the term "precursor cell" refers to a unipotent regenerative cell with the potential to differentiate into one cell type that performs one or more specific functions and may retain extensive proliferative capacity that enables the cells to proliferate under appropriate conditions. Exemplary examples of precursor cells include, without limitation, adipoblast (lipoblast or preadipocytes), de-differentiated adipocytes, angioblasts, endothelial precursor cells, fibroblasts, lymphoblasts, and macrophages.

Harvested adipose tissue can be supplemented with regenerative cells such as, e.g., stem cells, progenitor cells, and precursor cells. Regenerative cells may promote new blood vessel formation, diminish necrosis, and/or promote a supportive microenvironment in the transplanted tissue, thereby improving survivability of the transplanted tissue. Regenerative cells can be obtained from a variety of sources. For example, adipose tissue is rich in regenerative cells that have the ability to restore and reconstruct various soft tissue defects in response to local differentiation clues from the recipient site. As such, a portion of the collected adipose tissue may be further processed in order to purify regenerative cells that can then be added back to the remainder of the harvested adipose tissue in order to enrich this material for these cells. Exemplary methods describing such cell enrichment procedures can be found in, e.g., Hedrick and Fraser, Methods of Using Adipose Tissue-Derived Cells in Augmenting Autologous Fat Transfer, U.S. Patent Publication 2005/0025755, Yoshimura, et al., Characterization of Freshly Isolated and Cultured Cells Derived from the Fatty and Fluid Portions of liposuction Aspirates, J. Cell. Physiol. 208: 1011-1041 (2006); Yoshimura, et al., Cell-Assisted Lipotransfer for Facial Lipoatrophy: Effects of Clinical Use of Adipose-Derived Stem Cells, Dermatol. Surg. 34: 1178-1185 (2008); Yoshimura, et al., Cell-Assisted Lipotransfer for Cosmetic Breast Augmentation: Supportive Use of Adipose-Derived Stem/Stromal Cells, Aesth. Plast. Surg. 32: 48-55 (2008); each of which is hereby incorporated by reference in its entirety.

In addition, harvested adipose tissue can be supplemented with regenerative cells obtained from cell cultures, such as, e.g., primary cell cultures and established cell cultures. For example, a portion of harvested adipose tissue from an individual can be cultured in a manner to produce primary cell cultures enriched for regenerative cells. Alternatively, established cell lines derived from regenerative cells from adipose tissue, or another tissue source, can be cultured, harvested, and added to adipose tissue collected form an individual. Exemplary methods describing such cell culture compositions and procedures can be found in, e.g., Casteilla, et al., Method for Culturing Cells Derived from the Adipose Tissue and Uses Thereof, U.S. Patent Publication 2009/0246182; Chazenbalk, et al, Methods of Producing Preadipocytes and Increasing the Proliferation of Adult Adipose Stem/Progenitor Cells, U.S. Patent Publication 2009/0317367; Kleinsek and Soto, Augmentation and Repair of Sphincter Defects with Cells Including Adipocytic Cells, U.S. Patent Publication 2008/0299213; Rehman, et al., Secretion of Angiogenic and Antiapoptotic Factors by Human Adipose Stromal Cells, Circulation 109: r52-r58 (2004); Kilroy, et al., Cytokine Profile of Human Adipose-Derived Stem Cells: Expression of Angiogenic, Hematopoietic, and Pro-Inflammatory Factors, J. Cell. Physiol. 212: 702-709 (2007); each of which is hereby incorporated by reference in its entirety.

Harvested adipose tissue may be immediately used to make the compositions disclosed herein. Alternatively, harvested adipose tissue, whether unprocessed or processed, may be stored for used at some future date. Harvested tissue is typically stored using a slow freezing method of the tissue to −20° C., with or without cryopreservatives. Stored adipose tissue can typically be stored for at least 6 months.

Aspects of the present specification provide, in part, a composition comprising a compound having the structure of formula I

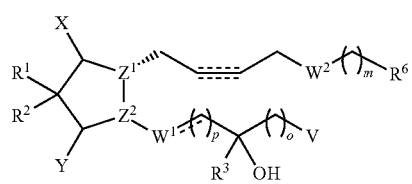

wherein each dashed line represents the presence or absence of a bond; $R^1$, $R^2$ and $R^3$ are each independently selected from H or $C_1$-$C_6$ alkyl; $R^6$ is $CO_2H$, $CO_2R^7$, $CON(R^7)_2$, $CONHCH_2CH_2OH$, $CON(CH_2CH_2OH)_2$, $CH_2OR^7$, $P(O)(OR^7)_2$, or

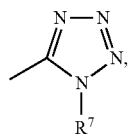

a pharmaceutically acceptable salt thereof, or a pharmaceutically acceptable amine salt thereof; $R^7$ is H, $C_1$-$C_6$ alkyl or $C_2$-$C_6$ alkenyl; X and Y are each independently selected from H, OH, =O, Cl, Br, I, or $CF_3$; $Z^1$ and $Z^2$ are each independently selected from CH or N; $W^1$ and $W^2$ are each independently selected from CH, $CH_2$, aryl or substituted aryl, heteroaryl, substituted heteroaryl; m is 0 to 6; o is 0 to 4; p is 0 or 1; and V is $C_1$-$C_6$ alkyl, aryl, substituted aryl, heteroaryl, or substituted heteroaryl.

The method of preparing the compounds represented by formula I can be found in, e.g., Donde, et al., 10,10-Dialkyl Prostanoic Acid Derivatives as Agents for Lowering Intraocular Pressure, U.S. Pat. No. 6,875,787; Donde, et al., 10,10-Dialkyl Prostanoic Acid Derivatives as Agents for Lowering Intraocular Pressure, U.S. Patent Publication 2004/0235958; Donde, et al., Treatment of Inflammatory Bowel Disease, U.S. Patent Publication 2005/0164992, each of which is hereby incorporated by reference in its entirety. See also companion applications Donde, et al., Compositions and Methods for Skin Repair, U.S. Provisional Patent Application 61/374,439; and Donde, et al., Compositions and Methods for Treating Corneal Haze, U.S. Provisional Patent Application 61/369,232; each of which is incorporated by reference in its entirety.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

In all of the disclosed structures, straight lines represent bonds, and where there is no symbol for the atoms between the bonds, the appropriate carbon-containing radical is to be inferred.

As used herein, the term "alkenyl" refers to a functional group comprising a straight-chain or branched-chain hydrocarbon containing from 2 to 20 carbon atoms and having one or more carbon-carbon double bonds and not having any cyclic structure. An alkenyl group may be optionally substituted as defined herein. Examples of alkenyl groups include, without limitation, ethenyl, propenyl, 2-methylpropenyl, butenyl, 1,4-butadienyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, and the like.

As used herein, the term "alkyl" refers to a functional group comprising a straight-chain or branched-chain hydrocarbon containing from 1 to 20 carbon atoms linked exclusively by single bonds and not having any cyclic structure. An alkyl group may be optionally substituted as defined herein. Examples of alkyl groups includes, without limitation methyl, ethyl, n-propyl, isopropyl, n-butyl, isobutyl, sec-butyl, tert-butyl, pentyl, iso-amyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and the like.

As used herein, the term "heteroalkyl" refers to a functional group comprising a straight-chain or branched-chain hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms may be consecutive, such as, e.g., —$CH_2$—NH—$OCH_3$. In addition, the non-carbon atoms may optionally be oxidized and the nitrogen may optionally be quaternized.

As used herein, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

As used herein, the term "amide" refers to a molecule comprising a carboxamide group [—C(=O)$NH_2$] and having the general formula RCONR'R", wherein R, R', and R" are an organic moiety or group.

As used herein, the term "amidine" refers to the functional group —C(=NH)$NH_2$.

As used herein, the term "amido" and "carbamoyl" refer to a functional group comprising an amino group attached to the parent molecular moiety through a carbonyl group, or vice versa. As used herein, either alone or in combination, the term "C-amido" refers to a —C(=O)—$NR_2$ group, wherein R is an organic moiety or group. As used herein, either alone or in combination, the term "N-amido" refers to a RC(=O)NH— group, wherein R is an organic moiety or group.

As used herein, the term "amine" refers to a molecule comprising an amino group (—$NH_2$) or derivative thereof. A primary amine has the general formula of $RNH_2$, a secondary amine has the general formula of NHRR', a tertiary amine has the general formula of NRR'R", wherein R, R', and R" are an organic moiety or group.

As used herein, the term "amino" refers to the functional group —$NH_2$—.

As used herein, the term "aminoalkyl" refers to a functional group comprising an alkyl group attached to the parent molecular moiety through an amino group. An alkylamino group may be a mono- or dialkylated forming group such as, e.g., N-methylamino, N-ethylamino, N,N-dimethylamino, N,N-ethylmethylamino and the like.

As used herein, the term "aryl" or "aryl hydrocarbon" refers to a functional group comprising a substituted or unsubstituted aromatic hydrocarbon with a conjugated cyclic molecular ring structure of 3 to 12 carbon atoms. An aryl group can be monocyclic, bicyclic or polycyclic, and may optionally include one to three additional ring structures, such as, e.g., a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, tolyl, xylyl, anthracenyl, phenanthryl, azulenyl, biphenyl, naphthalenyl, 1-methylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl. In aspects of this embodiment, an aryl is a 3 carbon aryl, a 4 carbon aryl, a 5 carbon aryl, a 6 carbon aryl, a 7 carbon aryl, a 8 carbon aryl, a 9 carbon aryl, a 10 carbon aryl, a 11 carbon aryl, or a 12 carbon aryl.

As used herein, the term "lower aryl" refers to a functional group comprising a substituted or unsubstituted aromatic hydrocarbon with a conjugated cyclic molecular ring structure of 3 to 6 carbon atoms. Examples of lower aryl groups include, without limitation, phenyl and naphthyl. In aspects of this embodiment, a lower aryl is a 3 carbon aryl, a 4 carbon aryl, a 5 carbon aryl, or a 6 carbon aryl. In other aspects, a lower aryl is a 5 or 6 carbon aryl.

As used herein, the term "heteroaryl" refers to a functional group comprising a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like. In aspects of this embodiment, a heteroaryl is a 3 carbon heteroaryl, a 4 carbon heteroaryl, a 5 carbon heteroaryl, a 6 carbon heteroaryl, a 7 carbon heteroaryl, a 8 carbon heteroaryl, a 9 carbon heteroaryl, a 10 carbon heteroaryl, a 11 carbon heteroaryl, or a 12 carbon heteroaryl.

As used herein, the term "lower heteroaryl" refers to a functional group comprising a monocyclic or bicyclic, substituted or unsubstituted aromatic hydrocarbon with a conjugated cyclic molecular ring structure of 3 to 6 atoms, where at least one atom in the ring structure is a carbon and at least one atom in the ring structure is O, S, N, or any combination thereof. In aspects of this embodiment, a lower heteroaryl is a 3 carbon heteroaryl, a 4 carbon heteroaryl, a 5 carbon heteroaryl, or a 6 carbon heteroaryl. In other aspects, a lower heteroaryl is a 5 or 6 carbon heteroaryl.

As used herein, the term "cycloalkenyl" and "cycloolefin" refers to a functional group comprising a substituted or unsubstituted non-aromatic hydrocarbon with a non-conjugated cyclic molecular ring structure of 3 to 12 carbon atoms having at least one carbon-carbon double bond in the carbon ring structure. A cycloalkenyl group can be monocyclic, bicyclic or polycyclic, and may optionally include one to three additional ring structures, such as, e.g., an aryl, a heteroaryl, a cycloalkyl, a heterocycloalkyl, or a heterocycloalkenyl. Examples of such cycloalkenyl groups include, without limitation, cyclopropene, cyclobutene, 1,3-cyclobutadiene, cyclopentene, 1,3-cyclopentadiene, cyclohexene, 1,3-cyclohexadiene, 1,4-cyclohexadiene, cycloheptene. 1,3-cycloheptadiene, 1,4-cycloheptadiene, and 1,5-cycloheptadiene. In aspects of this embodiment, a cycloalkenyl is a 3 carbon cycloalkenyl, a 4 carbon cycloalkenyl, a 5 carbon cycloalkenyl, a 6 carbon cycloalkenyl, a 7 carbon cycloalkenyl, a 8 carbon cycloalkenyl, a 9 carbon cycloalkenyl, a 10 carbon cycloalkenyl, a 11 carbon cycloalkenyl, or a 12 carbon cycloalkenyl.

As used herein, the term "lower cycloalkenyl" refers to a functional group comprising a monocyclic substituted or unsubstituted non-aromatic hydrocarbon with a non-conjugated cyclic molecular ring structure of 3 to 6 carbon atoms having at least one carbon-carbon double bond in the carbon ring structure. In aspects of this embodiment, a lower cycloalkenyl is a 3 carbon cycloalkenyl, a 4 carbon cycloalkenyl, a 5 carbon cycloalkenyl, or a 6 carbon cycloalkenyl. In other aspects, a lower cycloalkenyl is a 5 or 6 carbon cycloalkenyl.

As used herein, the term "heterocycloalkenyl" refers to a functional group comprising a substituted or unsubstituted non-aromatic hydrocarbon with a non-conjugated cyclic molecular ring structure of 3 to 12 atoms having at least one double bond, where at least one atom in the ring structure is a carbon and at least one atom in the ring structure is O, S, N, or any combination thereof. The heterocycloalkenyl group can be unsaturated, fully saturated or contain from 1 to 3 degrees of unsaturation. A heterocycloalkenyl group can be monocyclic, bicyclic or polycyclic, and may optionally include one to three additional ring structures, such as, e.g., an aryl, a heteroaryl, a cycloalkyl, a heterocycloalkyl, or a cycloalkenyl. In aspects of this embodiment, a heterocycloalkenyl is a 3 carbon heterocycloalkenyl, a 4 carbon heterocycloalkenyl, a 5 carbon heterocycloalkenyl, a 6 carbon heterocycloalkenyl, a 7 carbon heterocycloalkenyl, a 8 carbon heterocycloalkenyl, a 9 carbon heterocycloalkenyl, a 10 carbon heterocycloalkenyl, a 11 carbon heterocycloalkenyl, or a 12 carbon heterocycloalkenyl.

As used herein, the term "lower heterocycloalkenyl" refers to a functional group comprising a monocyclic substituted or unsubstituted non-aromatic hydrocarbon with a non-conjugated cyclic molecular ring structure of 3 to 6 atoms having at least one double bond, where at least one atom in the ring structure is a carbon and at least one atom in the ring structure is O, S, N, or any combination thereof. In aspects of this embodiment, a lower heterocycloalkenyl is a 3 carbon heterocycloalkenyl, a 4 carbon heterocycloalkenyl, a 5 carbon heterocycloalkenyl, or a 6 carbon heterocycloalkenyl. In other aspects, a lower heterocycloalkenyl is a 5 or 6 carbon heterocycloalkenyl.

As used herein, the term "cycloalkyl", "carbocyclicalkyl", and "carbocyclealkyl" refers to a functional group comprising a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl. In aspects of this embodiment, a cycloalkyl is a 3 carbon cycloalkyl, a 4 carbon cycloalkyl, a 5 carbon cycloalkyl, a 6 carbon cycloalkyl, a 7 carbon cycloalkyl, a 8 carbon cycloalkyl, a 9 carbon cycloalkyl, a 10 carbon cycloalkyl, a 11 carbon cycloalkyl, or a 12 carbon cycloalkyl.

As used herein, the term "lower cycloalkyl" refers to a functional group comprising a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups include, without limitation, cyclopropyl, cyclobutyl, cyclopentyl, and cyclohexyl. In aspects of this embodiment, a lower cycloalkyl is a 3 carbon cycloalkyl, a 4 carbon cycloalkyl, a 5 carbon cycloalkyl, or a 6 carbon cycloalkyl. In other aspects, a lower cycloalkyl is a 5 or 6 carbon cycloalkyl.

As used herein, the term "heterocycloalkyl", "heterocyclicalkyl", and "heterocyclealkyl" refers to a functional group comprising a substituted or unsubstituted non-aromatic hydrocarbon with a non-conjugated cyclic molecular ring structure of 3 to 12 atoms linked exclusively with single bonds in the ring structure, where at least one atom in the ring structure is a carbon and at least one atom in the ring structure is O, S, N, or any combination thereof. The heterocycloalkyl group can be unsaturated, fully saturated or contain from 1 to 3 degrees of unsaturation. A heterocycloalkyl group can be monocyclic, bicyclic or polycyclic, and may optionally include one to three additional ring structures, such as, e.g., an aryl, a heteroaryl a cycloalkyl, a cycloalkenyl, or a heterocycloalkenyl. A heterocycle group may be optionally substituted unless specifically prohibited. Examples of such heterocycloalkyl groups include, without limitation, aziridinyl, azirinyl, diazirinyl, oxiranyl, oxirenyl, dioxiranyl, thiiranyl, thiirenyl, azetidinyl, azetyl, diazetidinyl, oxetanyl, oxetyl, dioxetanyl, dioxetenyl, thietanyl, thietyl, dithietanyl, dithietyl, pyrrolidinyl, pyrrolinyl, pyrrolyl, furanyl, dihydrofuranyl, tetrahydrofuranyl, tetrahydrothiophenyl, dihydrothiophenyl, thiophenyl, imidazolidinyl, pyrazolidinyl, imidazolyl, imidazolinyl, pyrazolyl, pyrazolinyl, oxazolidinyl, isoxazolidinyl, oxazolyl, oxazolinyl, isoxazolyl, isoxazolinyl, thiazolidinyl, isothiazolidinyl, thiazolyl, thiazolinyl, isothiazolyl, isothiazolinyl, dioxolanyl, 1,3-dioxanyl, 1,4-dioxanyl, dioxolanyl, 1,3-dioxolanyl, oxathiolanyl, dithiolanyl, triazolyl, dithiazolyl, furazanyl, oxadiazolyl, thiadiazolyl, tetrazolyl, piperidinyl, tetrahydropyridinyl, pyridinyl, dihydropyridinyl, dihydro[1,3]oxazolo[4,5-b]pyridinyl, pyranyl, tetrahydropyranyl, thianyl, thiopyranyl, piperazinyl, diazinyl, morpholinyl, thiomorpholinyl, oxazinyl, thiazinyl, dithianyl, dioxanyl, dioxinyl, triazinyl, trioxanyl, tetrazinyl, azepanyl, azepinyl, oxepanyl, oxepinyl, thiepanyl, thiepinyl, diazepinyl, thiazepinyl, azocanyl, azocinyl, oxecanyl, thiocanyl, and the like. In aspects of this embodiment, a heterocycloalkyl is a 3 carbon heterocycloalkyl, a 4 carbon heterocycloalkyl, a 5 carbon heterocycloalkyl, a 6 carbon heterocycloalkyl, a 7 carbon heterocycloalkyl, a 8 carbon heterocycloalkyl, a 9 carbon heterocycloalkyl, a 10 carbon heterocycloalkyl, a 11 carbon heterocycloalkyl, or a 12 carbon heterocycloalkyl.

As used herein, the term "lower heterocycloalkyl" refers to a functional group comprising a monocyclic substituted or unsubstituted non-aromatic hydrocarbon with a non-conjugated cyclic molecular ring structure of 3 to 6 atoms linked exclusively with single bonds in the ring structure, where at least one atom in the ring structure is a carbon and at least one atom in the ring structure is O, S, N, or any combination thereof. Lower heterocycloalkyls may be unsaturated. Examples of lower heterocycloalkyls include, without limitation, pyrrolidinyl, imidazolidinyl, pyrazolidinyl, piperidinyl, piperazinyl, and morpholinyl. In aspects of this embodiment, a lower heterocycloalkyl is a 3 carbon heterocycloalkyl, a 4 carbon heterocycloalkyl, a 5 carbon heterocycloalkyl, or a 6 carbon heterocycloalkyl. In other aspects, a lower heterocycloalkyl is a 5 or 6 carbon heterocycloalkyl.

As used herein, the term "functional group" refers to a specific group of atoms within a molecule that are responsible for the characteristic chemical reactions of those molecules.

As used herein, the term "halo" or "halogen" refers to the nonmetal elements fluorine (F), chlorine (Cl), bromine (Br), iodine (I), astatine (At) and ununseptium (Us).

As used herein, the term "hydroxy" refers to the functional group hydroxyl (—OH).

As used herein, the term "hydroxyalkyl" refers to a functional group comprising an alkyl group attached to the parent molecular moiety through a hydroxyl group, such as, e.g., hydroxymethyl or hydroxyethyl.

As used herein, the term "imidate" or "imino ether" refers to a molecule comprising an imine (C=N—) and having the general formula RN=C(OR')R", wherein R, R' and R" are an organic moiety or group.

As used herein, the term "imide" refers to a functional group comprising two carbonyl groups bound to nitrogen [—C(=O)NC(=O)—], and having the general formula RCONCOR', wherein R and R' are an organic moiety or group.

As used herein, the term "imine" refers to the functional group —C=NH—. A primary ketimine has the general formula RCNHR', a secondary ketimine has the general formula RCNR'R", a primary aldimine has the general formula RCNHH, and a secondary aldimine has the general formula RCNR'H, wherein R, R" and R" are an organic moiety or group.

As used herein, the term "imino" refers to the functional group =NH—.

As used herein, the term "iminohydroxy" refers to the functional group =N(OH) and its corresponding anion =N—O—.

As used herein, the term "lower" refers to a functional group or molecule containing from 1 to 6 carbon atoms, unless otherwise specifically defined.

As used herein, the term "nitrile" refers to a molecule comparing a cyano group (—C≡N), and having the general formula RCN, wherein R is an organic moiety or group.

As used herein, the term "nitrite" refers to the functional group —NO$_2^-$, and having the general formula RNO$_2^-$, wherein R is an organic moiety or group.

As used herein, the term "nitroso" refers to the functional group —N=O, and having the general formula RNO, wherein R is an organic moiety or group.

As used herein, the term "nitro" refers to the functional group —NO$_2$, and having the general formula RNO$_2$, wherein R is an organic moiety or group.

As used herein, the term "nitrate" refers to the functional group —NO$_3^-$, and having the general formula RNO$_3^-$, wherein R is an organic moiety or group.

As used herein, the term "oxo" refers to the functional group =O.

As used herein, the term "oxy" or "oxa" refer to the functional group —O—.

As used herein, the term "oxyalkyl" refers to a functional group comprising an alkyl group attached to the parent molecular moiety through an oxy group.

As used herein, the term "unsubstituted" refers to a functional group or molecule that has hydrogen atoms at every position on the parent chain of a hydrocarbon (e.g., —CH$_2$CH$_3$).

As used herein, the term "substituted" refers to a functional group or molecule that has at least one substituent replacing a hydrogen atom at a position on the parent chain of a hydrocarbon. A substituted group may be fully substituted (e.g., —CF$_2$CF$_3$), monosubstituted (e.g., —CH$_2$CH$_2$F) or substituted at a level anywhere in between fully substituted and monosubstituted (e.g., —CH$_2$CH$_2$F, —CHFCH$_2$F, —CH$_2$CHF$_2$, —CHFCHF$_2$).

As used herein, the term "substituent" refers to an atom or group of atoms substituted in place of a hydrogen atom on the parent chain of a hydrocarbon. Where substituents are recited without qualification as to substitution, both substituted and unsubstituted forms are encompassed. Examples of substituents include, without limitation, acetyl, acyl, acylamino, acyl halide, alkenyl, alkoxy, alkyl, alkylamino, alkylcarbonyl, alkyloxy, alkyloxo, alkylthio, alkynyl, amidine, amido, amino, aryl, arylamino, arylalkenyl, arylalkoxy, arylalkyl, arylalkynyl, arylalkanoyl, aryloxy, arylthio, azide, azo, benzo, carbamyl, carbonyl, carboxyl, carboxamide, carboxamidine, cyanate, cyano, cycloalkenyl, cycloalkyl, diene, cyclodiene, disulfanyl, enone, halide, halogen, haloalkenyl, haloalkoxy, haloalkyl, heteroalkyl, heteroaryl, heterocycloalkenyl, heterocycloalkyl, hydrazinyl, hydrogen, hydroperoxide, hydroxy, hydroxyalkyl, imide, imine, imino, iminohydroxy, isocyanato, isothiocyanato, isocyanate, isocyanide, isothiocyanate, keto, mercaptyl, nitrite, nitroso, nitro, nitrate, oxo, oxy, oxoalkyl, oxyalkyl, oxime, perhaloalkoxy, perhaloalkyl, peroxy, sulfanyl, sulfhydryl, sulfinyl, sulfonyl, sulfyl, sulfonamido, thioalkyl, thiocarbonyl, thiocarbamoyl, thiocyanate, isothiocyanate, thiocyanato, thioketo, trihalomethanesulfonamido, trihalomethoxy, and/or all lower forms therein.

As used herein, the term "optionally substituted" refers to a functional group or molecule that may be either substituted or unsubstituted. Different sets of optional substituents to a particular moiety may be defined as needed; in these cases, the optional substitution will be as defined, often immediately following the phrase, "optionally substituted with." An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in between fully substituted and monosubstituted (e.g., —CH$_2$CH$_2$F, —CHFCH$_2$F, —CH$_2$CHF$_2$, —CHFCHF$_2$).

In another embodiment, the compound has the structure of formula II,

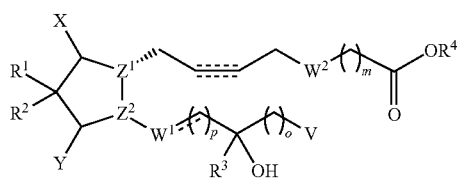

wherein each dashed line represents the presence or absence of a bond; $R^1$, $R^2$ and $R^3$ are each independently selected from H or $C_1$-$C_6$ alkyl; $R^4$ is H, $C_1$-$C_6$ alkyl, $C_2$-$C_6$ alkenyl, a pharmaceutically acceptable salt thereof, or a pharmaceutically acceptable amine salt thereof; X and Y are each independently selected from H, OH, =O, Cl, Br, I, or CF$_3$; $Z^1$ and $Z^2$ are each independently selected from CH or N; $W^1$ and $W^2$ are each independently selected from CH, CH$_2$, aryl or substituted aryl, heteroaryl, substituted heteroaryl; m is 0 to 4; o is 0 to 4; p is 0 or 1; and V is CH$_3$, aryl, aryl or substituted aryl, heteroaryl, substituted heteroaryl.

In an aspect of this embodiment, V is

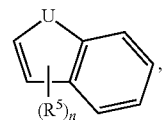

wherein U is C, N, O, or S; $R^5$ is halogen, $C_1$-$C_6$ alkyl, or $C_2$-$C_6$ alkenyl; and n is 0-7; and. In another aspect of this embodiment, U is S; $R^5$ is F, Cl, Br, or I; and n is 1, 2, or 3. In yet another aspect of this embodiment $W^2$ is thiophene.

In another embodiment, the compound has the structure of formula III,

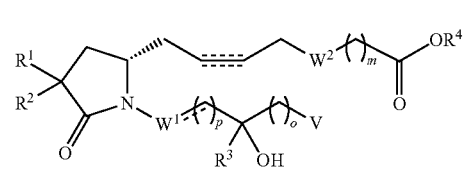

wherein each dashed line represents the presence or absence of a bond; $R^1$, $R^2$ and $R^3$ are each independently selected from H or $C_1$-$C_6$ alkyl; $R^4$ is H, $C_1$-$C_6$ alkyl, $C_2$-$C_6$ alkenyl, a pharmaceutically acceptable salt thereof, or a pharmaceutically acceptable amine salt thereof; $W^1$ and $W^2$ are each independently selected from CH, CH$_2$, aryl or substituted aryl, heteroaryl, substituted heteroaryl; m is 0 to 4; o is 0 to 4; p is 0 or 1; and V is CH$_3$, aryl, aryl or substituted aryl, heteroaryl, substituted heteroaryl.

In yet another embodiment, the compound has the structure of formula IV,

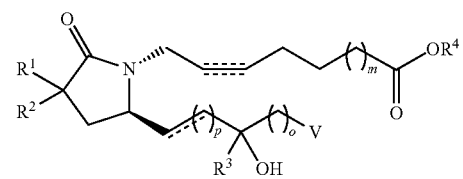

wherein each dashed line represents the presence or absence of a bond; $R^1$, $R^2$ and $R^3$ are each independently selected from H or $C_1$-$C_6$ linear alkyl; $R^4$ is H, $C_1$-$C_6$ alkyl, $C_2$-$C_6$ alkenyl, a pharmaceutically acceptable salt thereof, or a pharmaceutically acceptable amine salt thereof; m is 0 to 4; o is 0 to 4; p is 0 or 1; and V is CH$_3$, aryl, aryl or substituted aryl, heteroaryl, substituted heteroaryl.

In still another embodiment, the compound has the structure of formula V,

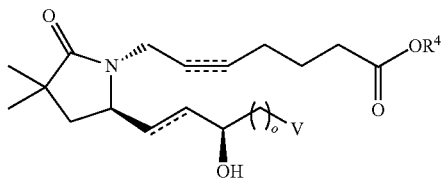

wherein each dashed line represents the presence or absence of a bond; $R^4$ is H, $C_1$-$C_6$ alkyl, $C_2$-$C_6$ alkenyl, a pharmaceutically acceptable salt thereof, or a pharmaceutically acceptable amine salt thereof; o is 0 to 4; and V is $CH_3$, aryl, aryl or substituted aryl, heteroaryl, substituted heteroaryl.

In a further embodiment, the compound has a structure of one of the following compounds listed in Table 1, a pharmaceutically acceptable salt thereof, or a pharmaceutically acceptable amine salt thereof.

TABLE 1

| Structure | Low $R_f$ diastereomer | High $R_f$ diastereomer |
|---|---|---|
| 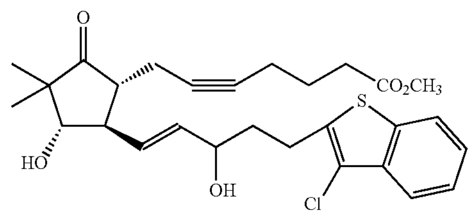 | 34 | 35 |
| 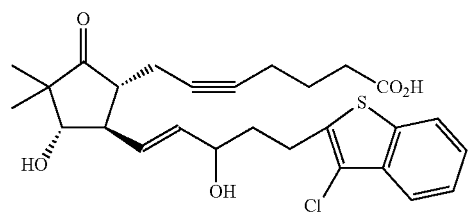 [SMILES: CC1(C)C(=O)[C@H](CC#CCCCC(=O)O)[C@@H](/C=C/C(O)CCc2sc3ccccc3c2Cl)[C@@H]1O] | 36 | 37 |
| 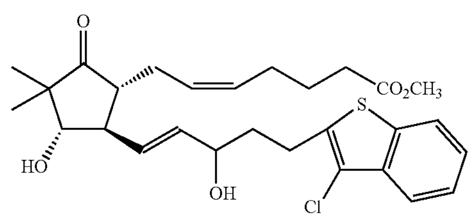 [SMILES: COC(=O)CCC/C=C\C[C@H]1C(=O)C(C)(C)[C@@H](O)[C@@H]1/C=C/C(O)CCc1sc2ccccc2c1Cl] | 38 | 39 |
| 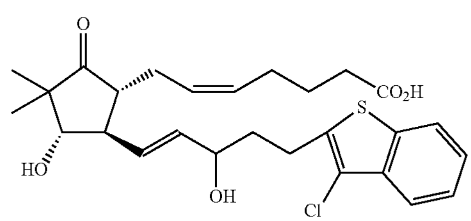 [SMILES: CC1(C)C(=O)[C@H](C/C=C\CCCC(=O)O)[C@@H](/C=C/C(O)CCc2sc3ccccc3c2Cl)[C@@H]1O] | 40 | 41 |
|  |  | 42 |

TABLE 1-continued

| Structure | Low R$_f$ diastereomer | High R$_f$ diastereomer |
|---|---|---|
| 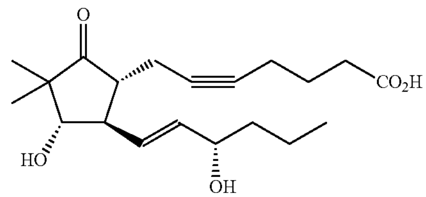 [SMILES: CCC[C@H](O)/C=C/[C@@H]1[C@@H](CC#CCCCC(=O)O)C(=O)C(C)(C)[C@H]1O] | 43 | |
| 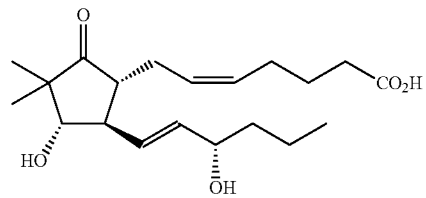 [SMILES: CCC[C@H](O)/C=C/[C@@H]1[C@@H](C/C=C\CCCC(=O)O)C(=O)C(C)(C)[C@H]1O] | 44 | |
| 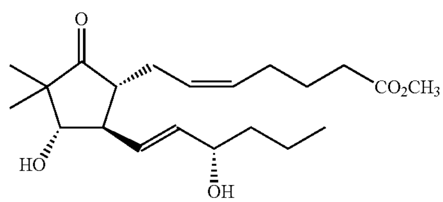 [SMILES: CCC[C@H](O)/C=C/[C@@H]1[C@@H](C/C=C\CCCC(=O)OC)C(=O)C(C)(C)[C@H]1O] | 45 | |
| 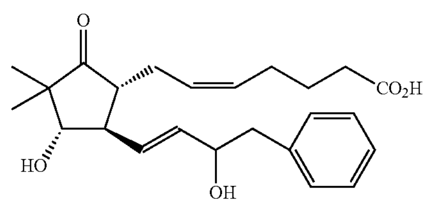 [SMILES: CC1(C)C(=O)[C@H](C/C=C\CCCC(=O)O)[C@@H](/C=C/C(O)Cc2ccccc2)[C@@H]1O] | 46 | 47 |
| 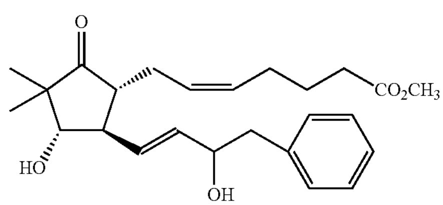 [SMILES: COC(=O)CCC/C=C\C[C@H]1C(=O)C(C)(C)[C@@H](O)[C@@H]1/C=C/C(O)Cc1ccccc1] | 48 | 49 |
| 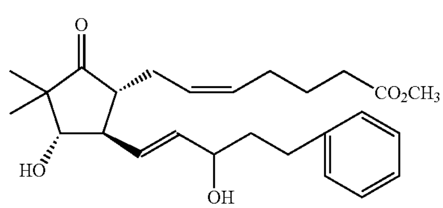 [SMILES: COC(=O)CCC/C=C\C[C@H]1C(=O)C(C)(C)[C@@H](O)[C@@H]1/C=C/C(O)CCc1ccccc1] | 50 | 51 |
| 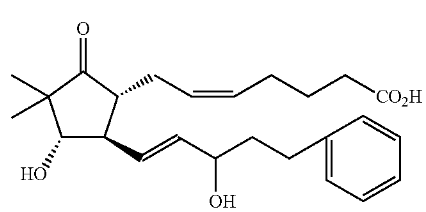 [SMILES: CC1(C)C(=O)[C@H](C/C=C\CCCC(=O)O)[C@@H](/C=C/C(O)CCc2ccccc2)[C@@H]1O] | 52 | 53 |

TABLE 1-continued
| Structure | Low R$_f$ diastereomer | High R$_f$ diastereomer |
|---|---|---|
| 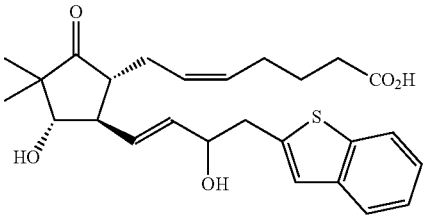 | 54 | 55 |
| 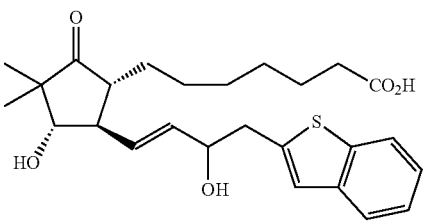 [SMILES: CC1(C)C(=O)[C@H](CCCCCCC(=O)O)[C@@H](/C=C/C(O)Cc2cc3ccccc3s2)[C@@H]1O] | 56 | 57 |
| 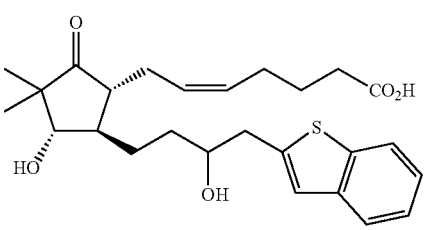 [SMILES: CC1(C)C(=O)[C@H](C/C=C\CCCC(=O)O)[C@@H](CCC(O)Cc2cc3ccccc3s2)[C@@H]1O] | 58 | 59 |
| 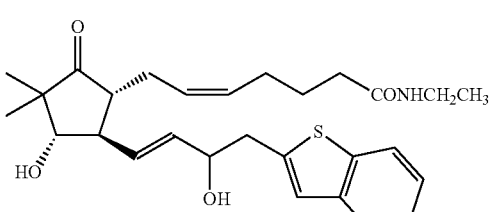 | 60 | 61 |
| 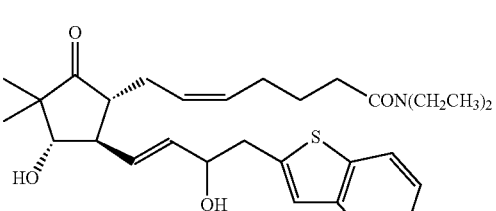 | 62 | 63 |
| 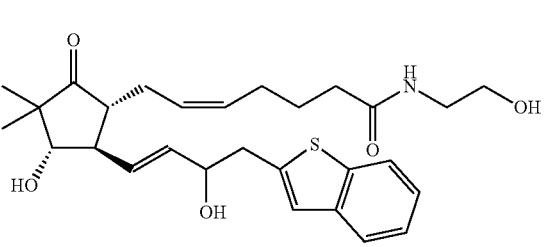 [SMILES: CC1(C)C(=O)[C@H](C/C=C\CCCC(=O)NCCO)[C@@H](/C=C/C(O)Cc2cc3ccccc3s2)[C@@H]1O] | 64 | 65 |

TABLE 1-continued
| Structure | Low R$_f$ diastereomer | High R$_f$ diastereomer |
| --- | --- | --- |
| 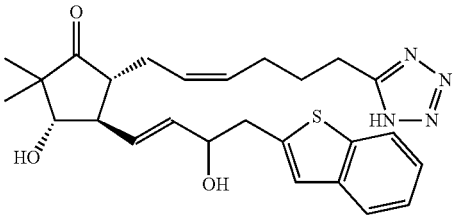 [SMILES: CC1(C)C(=O)[C@H](C/C=C\CCCc2nnn[nH]2)[C@@H](/C=C/C(O)Cc2cc3ccccc3s2)[C@@H]1O] | 66 | 67 |
| 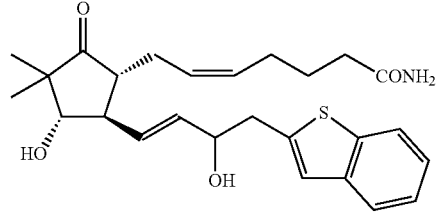 [SMILES: CC1(C)C(=O)[C@H](C/C=C\CCCC(N)=O)[C@@H](/C=C/C(O)Cc2cc3ccccc3s2)[C@@H]1O] | 68 | 69 |
| 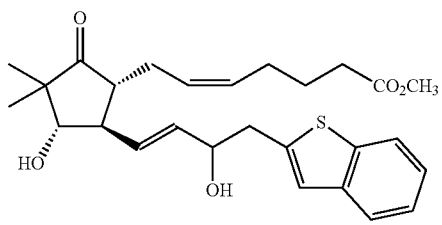 [SMILES: COC(=O)CCC/C=C\C[C@H]1C(=O)C(C)(C)[C@@H](O)[C@@H]1/C=C/C(O)Cc1cc2ccccc2s1] | 70 | 71 |
| 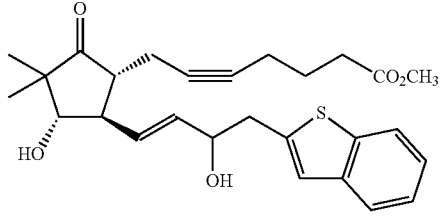 [SMILES: COC(=O)CCCC#CC[C@H]1C(=O)C(C)(C)[C@@H](O)[C@@H]1/C=C/C(O)Cc1cc2ccccc2s1] | 72 | 73 |
| 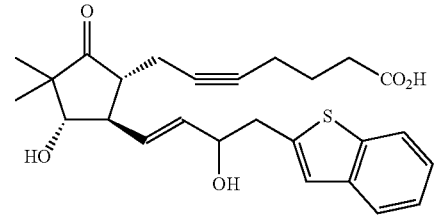 [SMILES: CC1(C)C(=O)[C@H](CC#CCCCC(=O)O)[C@@H](/C=C/C(O)Cc2cc3ccccc3s2)[C@@H]1O] | 74 | 75 |

In a further embodiment, the compound has a structure of compound 1, 2, 3, 4, or 5, a pharmaceutically acceptable salt thereof, or a pharmaceutically acceptable amine salt thereof.

In a yet further embodiment, the compound has a structure of compound 6, a pharmaceutically acceptable salt thereof, or a pharmaceutically acceptable amine salt thereof.

Compound 1

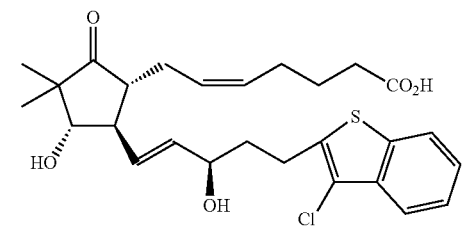

Compound 6

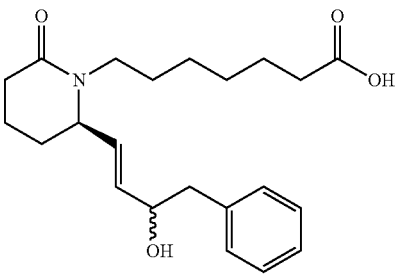

Compound 2

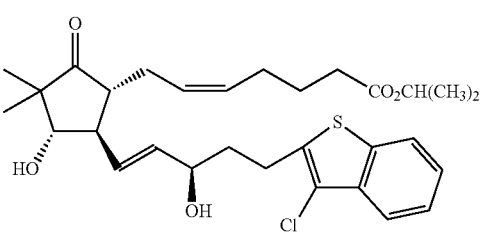

Coumpound 3

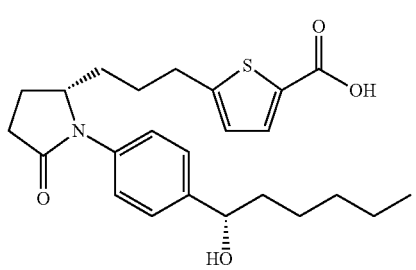

Compound 4

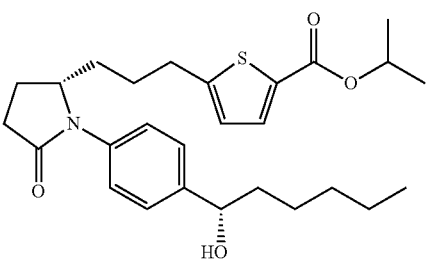

Compound 5

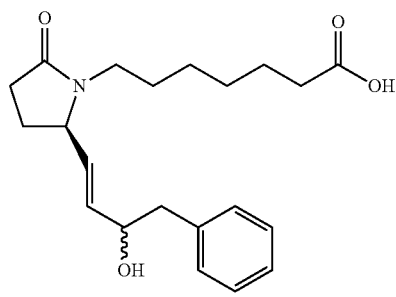

The compositions disclosed herein may, or may not, comprise any number and combination of compounds disclosed herein. For instance, a composition can comprise, e.g., two or more compounds, three or more compounds, four or more compounds or five or more compounds.

The addition of a compound to an adipose tissue may be accomplished by any method that ensures sufficient distribution of the compound throughout the adipose tissue so as to promote formation of a blood supply sufficient to support the transplanted tissue. For example, mixing may occur through automated means, such as, e.g., device-controlled agitation or centrifugation, or through manual methods, such as, e.g., luer-locked syringes or vortexing.

The compositions disclosed herein may, or may not, comprise one or more immunosuppressive agents that reduce, and preferably prevent, rejection of the transplanted tissue. As used herein, the term "immunosuppressive agent" is synonymous with "immunosuppressive drug" and refers to a compound that inhibits or interferes with normal immune function. Exemplary immunosuppressive agents suitable with the compositions and methods disclosed herein include, without limitation, agents that inhibit T-cell/B-cell costimulation pathways like agents that interfere with the coupling of T-cells and B-cells via the CTLA4 and B7 pathways, including cyclosporine A, mycophenolate mofetil, rapamycin, and anti-thymocyte globulin. An immunosuppressive drug is administered in a formulation that is compatible with the route of administration and is administered to an individual at a dosage sufficient to achieve the desired therapeutic effect.

A compound disclosed herein, or a composition comprising such a compound is generally administered to an individual as a pharmaceutical composition. Pharmaceutical compositions may be prepared by combining a therapeutically effective amount of at least one compound according to the present specification, or a pharmaceutically acceptable acid addition salt thereof, as an active ingredient, with conventional acceptable pharmaceutical excipients, and by preparation of unit dosage forms suitable for topical ocular use. The therapeutically efficient amount typically is between about 0.0001% (w/v) and about 5% (w/v), preferably about 0.001% (w/v) to about 1.0% (w/v) in liquid formulations. As used herein, the term "pharmaceutical composition" and refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

The compounds disclosed herein may also be incorporated into a drug delivery platform in order to achieve a controlled compound release profile over time. Such a drug delivery platform comprises a compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hydrophilic and Hydrophobic Agents, U.S. Pat. No. 7,048,946; Hughes, et al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. patent application Ser. No. 12/764,039, filed on Apr. 20, 2010; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

A pharmaceutical composition disclosed herein can optionally include a pharmaceutically acceptable carrier that facilitates processing of an active compound into pharmaceutically acceptable compositions. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNa-DTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

Aspects of the present specification provide, in part, a method of treating a soft tissue condition of an individual by administering a composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a compound disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A composition or compound is administered to an individual. An individual is typically a human being. Typically, any individual who is a candidate for a conventional soft tissue replacement procedure is a candidate for a soft tissue replacement procedure disclosed herein. In addition, the presently disclosed compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

The amount of adipose tissue used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of adipose tissue administration may be manifested by one or more of the following clinical and/or cosmetic measures: altered and/or improved soft tissue shape, altered and/or improved soft tissue size, altered and/or improved soft tissue contour, altered and/or improved tissue function, improved transplant tissue survival, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

The amount of a compound used with any of the methods disclosed herein will typically be a therapeutically effective amount. As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As a non-limiting example, an effective amount is an amount sufficient to promote formation of a blood supply sufficient to support the transplanted tissue. As another non-limiting example, an effective amount is an amount sufficient to promote formation of new blood vessels and associated vasculature (angiogenesis) and/or an amount sufficient to promote repair or remodeling of existing blood vessels and associated vasculature. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

In aspects of this embodiment, the amount of a compound added is, e.g., 0.01 mg, 0.05 mg, 0.1 mg, 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 500 mg, 750 mg, or 1000 mg. In other aspects of this embodiment, the amount of a compound added is, e.g., 0.01 mg/mL, 0.05 mg/mL, 0.1 mg/mL, 0.5 mg/mL, 1 mg/mL, 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 500 mg/mL, 750 mg/mL, or 1000 mg/mL. In yet other aspects of this embodiment, the amount of a compound added is, e.g., 0.01 mg/10 mL of tissue, 0.05 mg/10 mL of tissue, 0.1 mg/10 mL of tissue, 0.5 mg/10 mL of tissue, 1 mg/10 mL of tissue, 5 mg/10 mL of tissue, 10 mg/10 mL of tissue, 20 mg/10 mL of tissue, 30 mg/10 mL of tissue, 40 mg/10 mL of tissue, 50 mg/10 mL of tissue, 60 mg/10 mL of tissue, 70 mg/10 mL of tissue, 80 mg/10 mL of tissue, 90 mg/10 mL of tissue, 100 mg/10 mL of tissue, 150 mg/10 mL of tissue, 200 mg/10 mL of tissue, 250 mg/10 mL of tissue, 500 mg/10 mL of tissue, 750 mg/10 mL of tissue, or 1000 mg/10 mL of tissue.

In aspects of this embodiment, the amount of a compound added is, e.g., about 0.01 mg to about 0.1 mg, about 0.1 mg to about 1 mg, about 1 mg to about 10 mg, about 10 mg to about 100 mg, or about 100 mg to about 1000 mg. In other aspects of this embodiment, the amount of a compound added is, e.g., about 0.01 mg/mL to about 0.1 mg/mL, about 0.1 mg/mL to about 1 mg/mL, about 1 mg/mL to about 10 mg/mL, about 10 mg/mL to about 100 mg/mL, or about 100 mg/mL to about 1000 mg/mL. In yet other aspects of this embodiment, the amount of a compound added is, e.g., about 0.01 mg/10 mL of tissue to about 0.1 mg/10 mL of tissue, about 0.1 mg/10 mL of tissue to about 1 mg/10 mL of tissue, about 1 mg/10 mL of tissue to about 10 mg/10 mL of tissue, about 10 mg/10 mL of tissue to about 100 mg/10 mL of tissue, or about 100 mg/10 mL of tissue to about 1000 mg/10 mL of tissue.

In aspects of this embodiment, the amount of a compound added is, e.g., about 0.0001% (w/v) to about 5% (w/v), about 0.001% (w/v) to about 5% (w/v), about 0.01% (w/v) to about 5% (w/v), about 0.1% (w/v) to about 5% (w/v), or about 1% (w/v) to about 5% (w/v). In other aspects of this embodiment, the amount of a compound added is, e.g., about 0.001% (w/v) to about 1.0% (w/v), about 0.01% (w/v) to about 1.0% (w/v), or about 0.1% (w/v) to about 1.0% (w/v).

The route of administration of composition administered to an individual patient will typically be determined based on the cosmetic and/or clinical effect desired by the individual and/or physician and the body part or region being treated. Compositions or adipose tissue may be administered by any means known to persons of ordinary skill in the art including, without limitation, syringe with needle, catheter, or by direct surgical implantation. In addition, composition or adipose tissue can be administered once, or over a plurality of times. Ultimately, the timing used will follow quality care standards.

For a breast soft tissue replacement procedure, the route of administration may include axillary, periareolar, and/or inframammary routes. For a facial soft tissue replacement procedure, the route of administration can be frontal, temporal, zygomatic, periocular, mandibula, perioral or chin routes. In urinary incontinence procedures, the route of administration may include transurethral or periurethral routes. Alternatively or in addition, the transplant may be delivered via an antegrade route. The routes discussed herein do not exclude the use of multiple routes to achieve the desired clinical effect, or umbilical incision. Alternatively or in addition, cell-enhanced tissue may be delivered through a transaxillary endoscopic subpectoral approach.

A composition or compound administered to an individual to treat a soft tissue condition promotes formation of a blood supply sufficient to support the transplanted tissue. Blood supply formation includes, without limitation, formation of new blood vessels and associated vasculature (angiogenesis) and repair or remodel of existing blood vessels and associated vasculature.

Aspects of the present specification disclose, in part, a method of treating a soft tissue condition of an individual, the method comprising the steps of a) administering the adipose tissue to a site of the soft tissue condition; and b) administering a composition comprising a compound as disclosed herein to the site of the soft tissue condition. The adipose tissue and compounds administered includes the adipose tissue disclosed herein. In these methods, the adipose tissue is administered separately from a composition comprising the compound. Thus, in one aspect of this embodiment, adipose tissue is administered first, following by administration of a composition comprising the compound. In another aspect of this embodiment, a composition comprising a compound is administered first, following by administration of adipose tissue.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compositions and methods of soft tissue replacement disclosed herein.

Example 1

Synthesis of Compounds of Formula I

This example illustrates the synthesis scheme for the compounds of formula I.

The methods of preparing the compounds disclosed herein are further illustrated by the following non-limiting examples, which are summarized in the reaction schemes of FIGS. 1-9 wherein the compounds are identified by the same designator in both the Examples and the Figures.

2-Alkyl-cyclopentane-1,3-dione (1a, FIG. 1)

A mixture of 1,3-cyclopentanedione (89.4 mmol, Aldrich), I—$R^2$ (96.4 mmol, Aldrich), and KOH (5.097 g, 90.8 mmol) in water (25 mL)/dioxane (75 mL) was heated at reflux. After 5 hours, a solution of KOH (2 g) and I—$R^2$ (2 mmol) in water (5 mL)/dioxane (15 mL) was added and after another 3 hours at reflux, the solution was stirred at room temperature overnight. A solution of KOH (2 g) and I—$R^2$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until boiling was observed (ca. 15 minutes). The mixture was cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2-Alkyl-2-methyl-cyclopentane-1,3-dione (2a, FIG. 1)

A mixture of 2-methyl-1,3-cyclopentanedione (10.025 g, 89.4 mmol, Aldrich), I—$R^2$ (96.4 mmol, Aldrich), and KOH (5.097 g, 90.8 mmol) in water (25 mL)/dioxane (75 mL) was heated at reflux. After 5 hours, a solution of KOH (2 g) and I—$R^2$ (2 mmol) in water (5 mL)/dioxane (15 mL) was added and after another 3 hours at reflux, the solution was stirred overnight at room temperature. A solution of KOH (2 g) and I—$R^2$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2,2-Dialkyl-methyl-cyclopentane-1,3-dione (2b, FIG. 1)

A mixture of 2-alkyl-1,3-cyclopentanedione 1a (89.4 mmol, Aldrich), I—$R^3$ (96.4 mmol, Aldrich), and KOH (5.097 g, 90.8 mmol) in water (25 mL)/dioxane (75 mL) was heated at reflux. After 5 hours, a solution of KOH (2 g) and I—$R^3$ (2 mmol) in water (5 mL)/dioxane (15 mL) was added and after another 3 hours at reflux, the solution was stirred at room temperature overnight. A solution of KOH (2 g) and I—$R^3$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was then cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

Spiro[2.4]heptane-4,7-dione (2c, FIG. 1)

A mixture of 2-alkyl-1,3-cyclopentanedione 1a (89.4 mmol, Aldrich), 1,2-dibromoethane (120 mmol, Aldrich), and KOH (5.097 g, 90.8 mmol) in water (25 mL)/dioxane (75 mL) was heated at reflux for 24 hours. The mixture was cooled, and the product extracted with ether (1×100 mL, 3×75 mL). The combined ether extracts were evaporated, the residue combined with 10% HCl (50 mL), and the resulting mixture placed in a 120° C. oil bath until boiling was observed (ca. 15 minutes). The mixture was then cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2,2-Dimethyl-cyclopentane-1,3-dione (2, FIG. 1)

Synthesized according to Agosta and Smith, J. Org. Chem. 35: 3856 (1970) A mixture of 2-methyl-1,3-cyclopentanedione (10.025 g, 89.4 mmol, Aldrich), methyl iodide (6.0 mL, 96.4 mmol, Aldrich), and KOH (5.097 g, 90.8 mmol) in water (25 mL)/dioxane (75 mL) was heated at reflux. After 5 hours, a solution of KOH (2 g) and MeI (2.4 mL) in water (5 mL)/dioxane (15 mL) was added and after another 3 hours at reflux, the solution was stirred at room temperature overnight. A solution of KOH (2 g) and MeI (2.4 mL) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was cooled to room temperature, neutralized by addition of saturated NaHCO$_3$ solution (150 mL) and the resulting mixture extracted with CH$_2$Cl$_2$ (4×75 mL). The combined CH$_2$Cl$_2$ solution was dried (MgSO$_4$), filtered and evaporated to leave a brown oil (10.474 g, 83 mmol, 93%) which was used directly in the next step.

Figure 2:
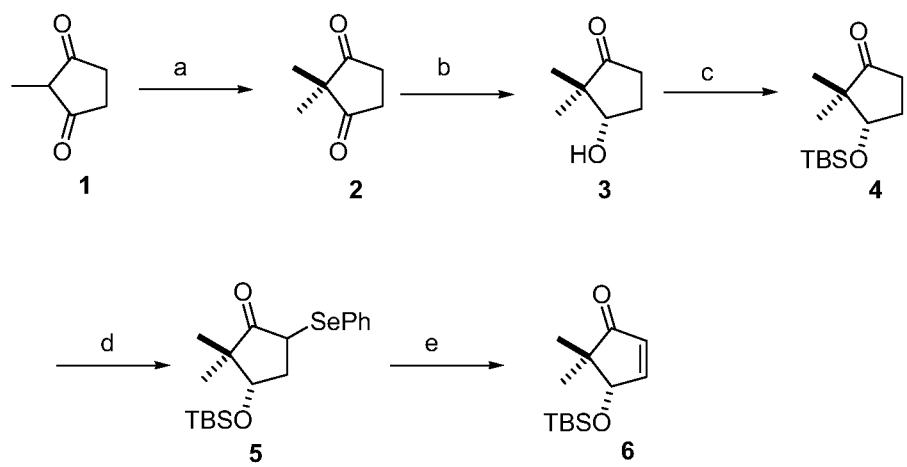

(S)-3-Hydroxy-2,2-dimethyl-cyclopentanone (3, FIG. 2)

Synthesized according to Brooks, et al., J. Org. Chem. 52: 3223 (1987). A 35° C. (internal temperature) solution of D-glucose (106.73 g, 592 mmol, Aldrich) in water (690 mL) in a 4 L Erlenmeyer was treated with baker's yeast (71.065 g, Fleischmann's). The mixture was fermented for 2 hours, and 2,2-dimethyl-cyclopentane-1,3-dione (2) (7.316 g, 58 mmol) was added. The mixture was stirred for 48 hours and filtered through celite, washing with about 1 L CH$_2$Cl$_2$. About 100 mL of brine was added to the filtrate and the layers separated using a separatory funnel. Brine (400 mL) was added to the aqueous layer and the resulting solution extracted further with CH$_2$Cl$_2$ (3×500 mL). The combined CH$_2$Cl$_2$ solution was dried (MgSO$_4$), filtered and evaporated to leave a yellow oil. Flash chromatography (11×5 cm, 20% EtOAc/hexs→25→30→40→50%) gave alcohol 3 (2.435 g, 19 mmol, 33%).

The enantiomeric excess of 3 was assayed by $^1$H NMR of the corresponding Mosher's ester which was prepared by treatment of alcohol 3 (11 mg, 0.09 mmol) in dichloroethane (0.3 mL, Aldrich) with pyridine (27 µL, 0.33 mmol, Aldrich) and (R)-α-methoxy-α-trifluoromethylphenylacetic acid chloride (58 µL, 0.31 mmol, Fluka). The mixture was stirred overnight and then partitioned between water (10 mL) and ether (10 mL). The ether layer was washed with 1 M HCl (10 mL) and saturated NaHCO$_3$ solution and then dried (MgSO$_4$), filtered and evaporated. $^1$H NMR analysis was done on the crude ester.

(S)-3-(tert)-Butyl-dimethyl-silanyloxy-2,2-dimethyl-cyclopentanone (4, FIG. 2)

A solution of alcohol (3) (520 mg, 4.1 mmol) and 2,6-lutidine (0.56 mL, 4.8 mmol, Aldrich) in CH$_2$Cl$_2$ (8.0 mL, Aldrich) was treated with TBSOTf (1.0 mL, 4.3 mmol, Aldrich). After 5.5 hours, saturated NaHCO$_3$ solution (20 mL) was added and the mixture extracted with CH$_2$Cl$_2$ (20 mL). The CH$_2$Cl$_2$ solution was washed with 20 mL each of 1 M HCl, saturated NaHCO$_3$ solution, and brine and then dried (MgSO$_4$), filtered and evaporated. Flash chromatography (5×5 cm, 10% Et$_2$O/pentane) gave TBS ether (4) (698 mg, 2.9 mmol, 70%).

(S)-3-(tert)-Butyl-dimethyl-silanyloxy-2,2-dimethyl-5-phenylselanyl-cyclopentanone (5, FIG. 2)

A solution of TBS ether (4) (1.496 g, 6.2 mmol) in THF (2 mL, Aldrich) was added dropwise to a −78° C. solution of LDA (4.9 mL, 7.3 mmol, 1.5 M/cyclohexane, Aldrich) in THF (22 mL, Aldrich), rinsing with 2 mL THF. After 15 minutes, a solution of PhSeCl (1.424 g, 7.4 mmol, Aldrich) in THF (2 mL) was quickly added by cannula, rinsing with 2 mL THF. The solution was stirred for 10 minutes and then partitioned between 50 mL 0.5 M HCl and 75 mL ether. The ether layer was washed with 30 mL each of water, saturated NaHCO$_3$ solution, and brine and then dried (MgSO$_4$), filtered and evaporated. Flash chromatography (2% EtOAc/hexs→4%) gave phenylselenide (5) (1.641 g, 4.1 mmol, 67%) along with 476 mg of mixed fractions containing a lower R$_f$ impurity.

(S)-4-(tert)-Butyl-dimethyl-silanyloxy-5,5-dimethyl-cyclopent-2-enone (6, FIG. 2)

A solution of selenide (5) (1.641 g, 4.1 mmol) and pyridine (0.62 mL, 7.7 mmol, Aldrich) in CH$_2$Cl$_2$ (13 mL, Aldrich) was treated with water (1 mL) and 30% H$_2$O$_2$ (1.1 mL, Aldrich). The mixture was stirred for 30 minutes and then partitioned between 25 mL CH$_2$Cl$_2$ and 25 mL saturated NaHCO$_3$ solution. The aqueous layer was extracted with 25 mL CH$_2$Cl$_2$ and the combined CH$_2$Cl$_2$ solution washed with 1 M HCl (2×25 mL) and brine (50 mL). The solution was dried (MgSO$_4$), filtered and evaporated to leave an orange oil. Flash chromatography (6×4 cm, 10% ether/pentane) gave enone (6) (572 mg, 2.4 mmol, 59%).

Figure 3:
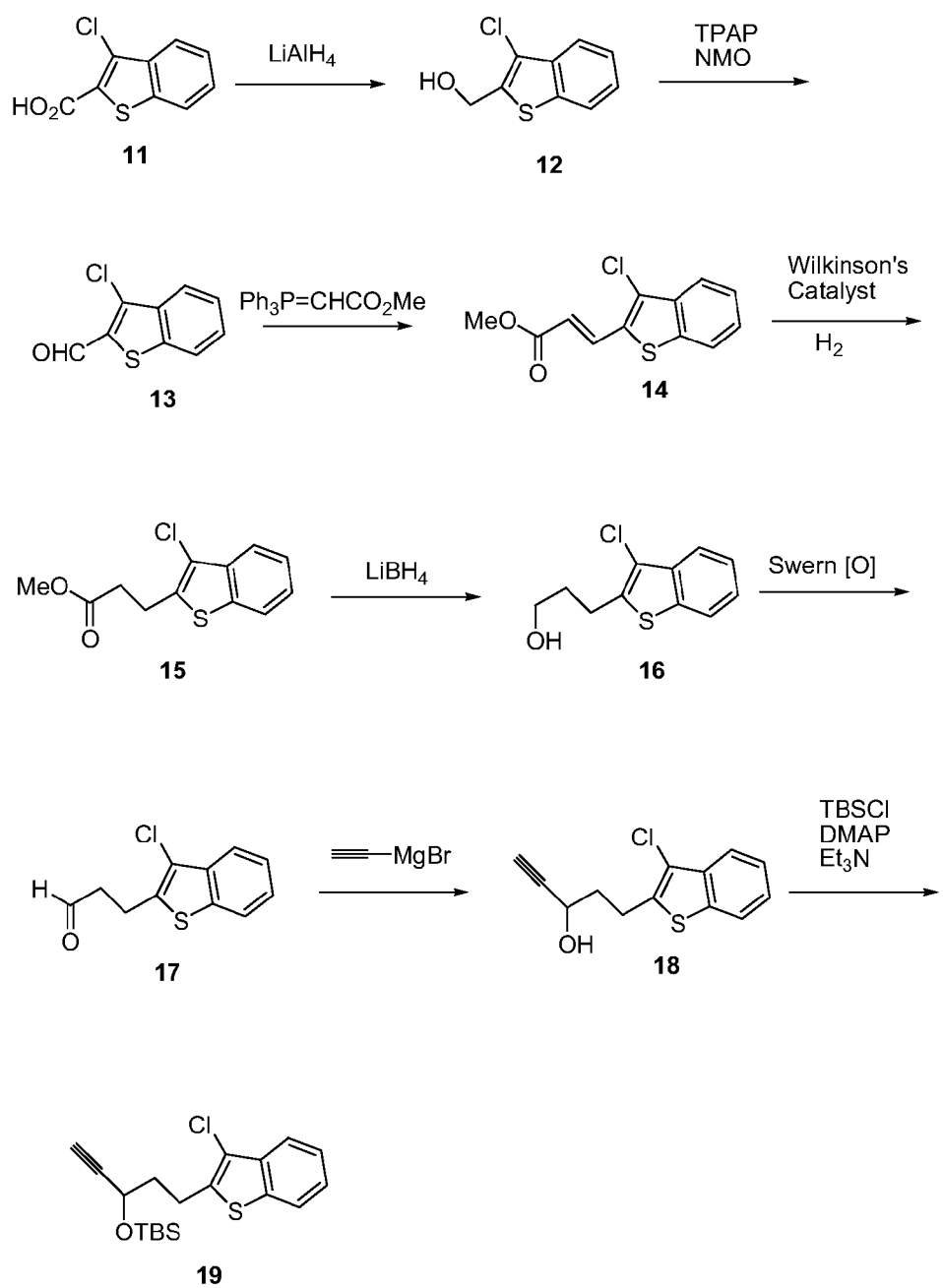

(3-Chloro-benzo[b]thiophen-2-yl)-methanol (12, FIG. 3)

To an ice cold solution of 10.0 g (47.0 mmol) of 3-chloro-benzo[b]thiophene-2-carboxylic acid (11) in 200 mL of THF was added 47 mL of LiAlH$_4$ (47 mmol, 1 M/THF). After 3 hours, the reaction was quenched by adding methanol (ca. 40 mL). The volatiles were evaporated and the residue treated with 50 mL 1 M HCl. After stirring for 10 minutes, the mixture was extracted with CH$_2$Cl$_2$ (3×150 mL). The combined CH$_2$Cl$_2$ solution was dried (MgSO$_4$), filtered and evaporated. Purification by flash chromatography on silica gel (10-20% ethyl acetate/hexane) gave 4.32 g (21.6 mmol, 46%) of the alcohol (12).

3-Chloro-benzo[b]thiophene-2-carbaldehyde (13, FIG. 3)

A solution of alcohol 12 (4.32 g, 21.6 mmol) in 40 mL of CH$_2$Cl$_2$ was treated with 4 A molecular sieves, NMO (3.81 g, 32.5 mmol), and TPAP (381 mg, 1.08 mmol). The reaction was stirred for 10 minutes and then dried by evaporated. Purification by flash chromatography on silica gel (2% ethyl acetate/hexane) gave 3.52 g (18.3 mmol, 84%) of the aldehyde (13).

(E)-3-(3-Chloro-benzo[b]thiophen-2-yl)-acrylic acid methyl ester (14, FIG. 3)

A solution of 3.52 g (18.3 mmol) of (13) in 50 mL toluene was treated with methyl(triphenylphosphoranylidene)acetate (7.48 g, 21.9 mmol). After 4 hours, saturated NaHCO$_3$ solution (50 mL) was added and the mixture extracted with ethyl acetate (2×75 mL). The combined ethyl acetate solution was washed with brine (50 mL), dried (Na$_2$SO$_4$), filtered and evaporated. Purification by flash chromatography on silica gel (5% ethyl acetate/hexane) provided 3.60 g (14.6 mmol, 80%) of the enoate (14).

3-(3-Chloro-benzo[b]thiophen-2-yl)-propionic acid methyl ester (15, FIG. 3)

A solution of 3.60 g (14.6 mmol) of (14) in 50 mL THF was treated with Wilkinson's catalyst (3.35 g, 3.62 mmol). The mixture was stirred under 1 atm H$_2$ for 18 hours and then was filtered through celite. The solvent was evaporated and the residue purified by flash chromatography on silica gel (0-2% ethyl acetate/hexane) to give 3.63 g (14.3 mmol, 99%) of the saturated ester (15).

3-(3-Chloro-benzo[b]thiophen-2-yl)-propan-1-ol (16, FIG. 3)

An ice cold solution of 3.63 g (14.3 mmol) of (15) in 60 mL of ether was treated with LiBH$_4$ (621 mg, 28.5 mmol) and methanol (2 mL). After 30 minutes, 30 mL of 0.5 M NaOH solution was added. The mixture was extracted with ethyl acetate (2×25 mL) and the combined ethyl acetate solution was washed with brine (50 mL), dried (MgSO$_4$), filtered and evaporated. The residue was purified by flash chromatography on silica gel (5-20% ethyl acetate/hexane) to give 2.57 g (11.3 mmol, 79%) of the alcohol (16).

3-(3-Chloro-benzo[b]thiophen-2-yl)-propionaldehyde (17, FIG. 3)

A −78° C. solution of oxalyl chloride (1.73 g, 13.6 mmol) in dichloromethane (20 mL) was treated with DMSO (20 mL). After 5 minutes, a solution of alcohol (16) (2.57 g, 11.3 mmol) in dichloromethane (20 mL) was added. After another 15 minutes, triethylamine (7.1 mL, 50.6 mmol) was added. The reaction was stirred at −78° C. for 5 minutes, and warmed to room temperature. After 30 minutes, 100 mL water was added and the mixture extracted with dichloromethane (3×60 mL). The combined dichloromethane solution was dried (Na$_2$SO$_4$), filtered and evaporated. Purification by flash chromatography on silica gel (10% ethyl acetate/hexane) gave 2.11 g (9.4 mmol, 83%) of the aldehyde (17).

5-(3-Chloro-benzo[b]thiophen-2-yl)-pent-1-yn-3-ol (18, FIG. 3)

A solution of aldehyde (17) (2.11 g, 9.4 mmol) in 15 mL THF was added to a solution of ethynylmagnesium bromide (28.2 mL, 14.1 mmol, 0.5 M THF) at 0° C. After 1.5 hours, saturated NH$_4$Cl solution (75 mL) was added and the mixture was extracted with ethyl acetate (3×50 mL). The combined ethyl acetate solution was washed with brine (50 mL) and then dried (Na$_2$SO$_4$), filtered and evaporated. Purification by flash chromatography (5-20% ethyl acetate/hexane) gave 2.20 g (8.78 mmol, 93%) of the alcohol (18).

tert-Butyl-{1-[2-(3-chloro-benzo[b]thiophen-2-yl)-ethyl]-prop-2-ynyloxy}-dimethyl-silane (19, FIG. 3)

Figure 4:
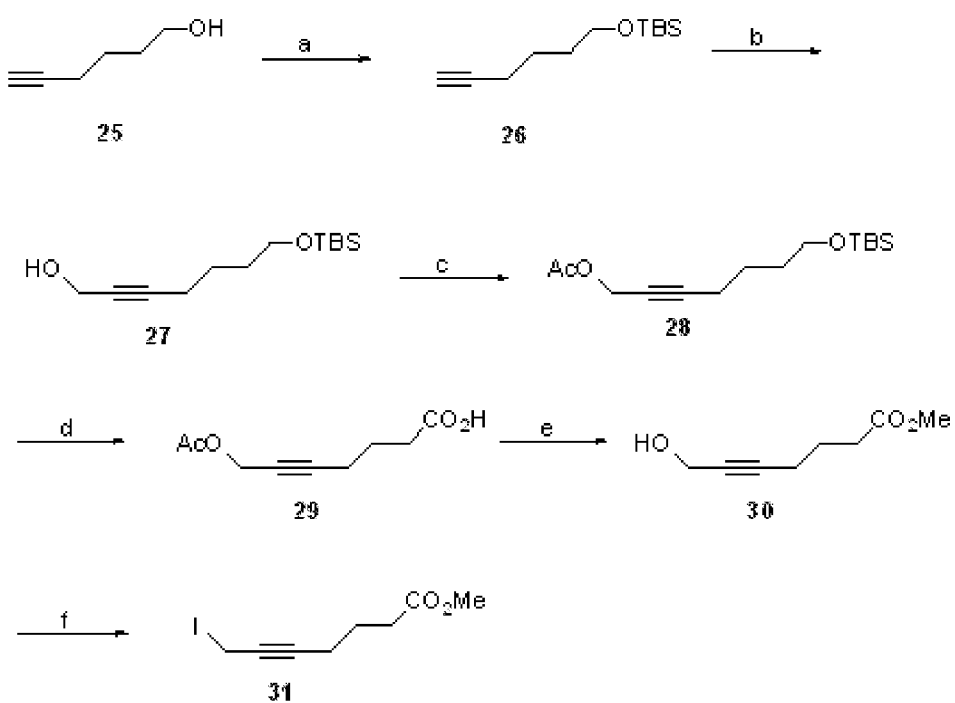

A solution of alcohol (18) (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 hours and then saturated sodium bicarbonate solution (50 mL) was added. The mixture was extracted with dichloromethane (2×50 mL) and the combined dichloromethane solution dried (Na$_2$SO$_4$), filtered and evaporated. Purification by flash chromatography (4% ethyl acetate/hexane) gave 3.06 g (6.4 mmol, 73%) of the protected alcohol (19).

tert-Butyl-hex-5-ynyloxy-dimethyl-silane (26); 7-(tert-Butyl-dimethyl-silanyloxy)-hept-2-yn-1-ol (27); and Acetic acid 7-(tert-butyl-dimethyl-silanyloxy)-hept-2-ynyl ester (28, FIG. 4)

A solution of 7-(tert-Butyl-dimethyl-silanyloxy)-hept-2-yn-1-ol (27) (4.507 g, 21 mmol) in pyridine (20 mL) was treated with acetic anhydride (3.0 mL, 31.8 mmol). After 18 hours, the solvent was evaporated and the residue co-evaporated with toluene. The residue was used directly in the next step.

7-Acetoxy-hept-5-ynoic acid (29, FIG. 4)

A solution of crude (28) in acetone (100 mL) was treated with Jones Reagent (18.0 mL, 41.4 mmol, 2.3 M) and cooled with an ice bath. After 1 hour at room temperature, 10 mL isopropyl alcohol was added and the mixture stirred for 15 minutes. The mixture still had a brown color so another 10 mL isopropyl alcohol was added. After another 15 minutes, the color had not changed so the mixture was filtered through celite and the filtrate evaporated in vacuo. The residue was partitioned between 100 mL ether and 100 mL saturated ammonium chloride solution. The aqueous layer was extracted with 100 mL ether and the combined ether solution washed with brine and then dried (MgSO$_4$), filtered and evaporated to leave a yellow oil (6.333 g) that was used directly in the next step.

7-Hydroxy-hept-5-ynoic acid methyl ester (30, FIG. 4)

The crude acid (29) (6.333 g) was treated with a 1% solution of acetyl chloride in methanol (60 mL). After 16 hours, sodium bicarbonate (1.966 g, 23.4 mmol) was added. The mixture was dried (MgSO$_4$), filtered through celite and evaporated in vacuo. Purification by flash chromatography on silica gel (30-40% ethyl acetate/hexanes) gave 7-Hydroxy-hept-5-ynoic acid methyl ester (30) (3.022 g, 19.3 mmol, 92% from 7-(tert-Butyl-dimethyl-silanyloxy)-hept-2-yn-1-ol (27).

7-Iodo-hept-5-ynoic acid methyl ester (31, FIG. 4)

Figure 5:
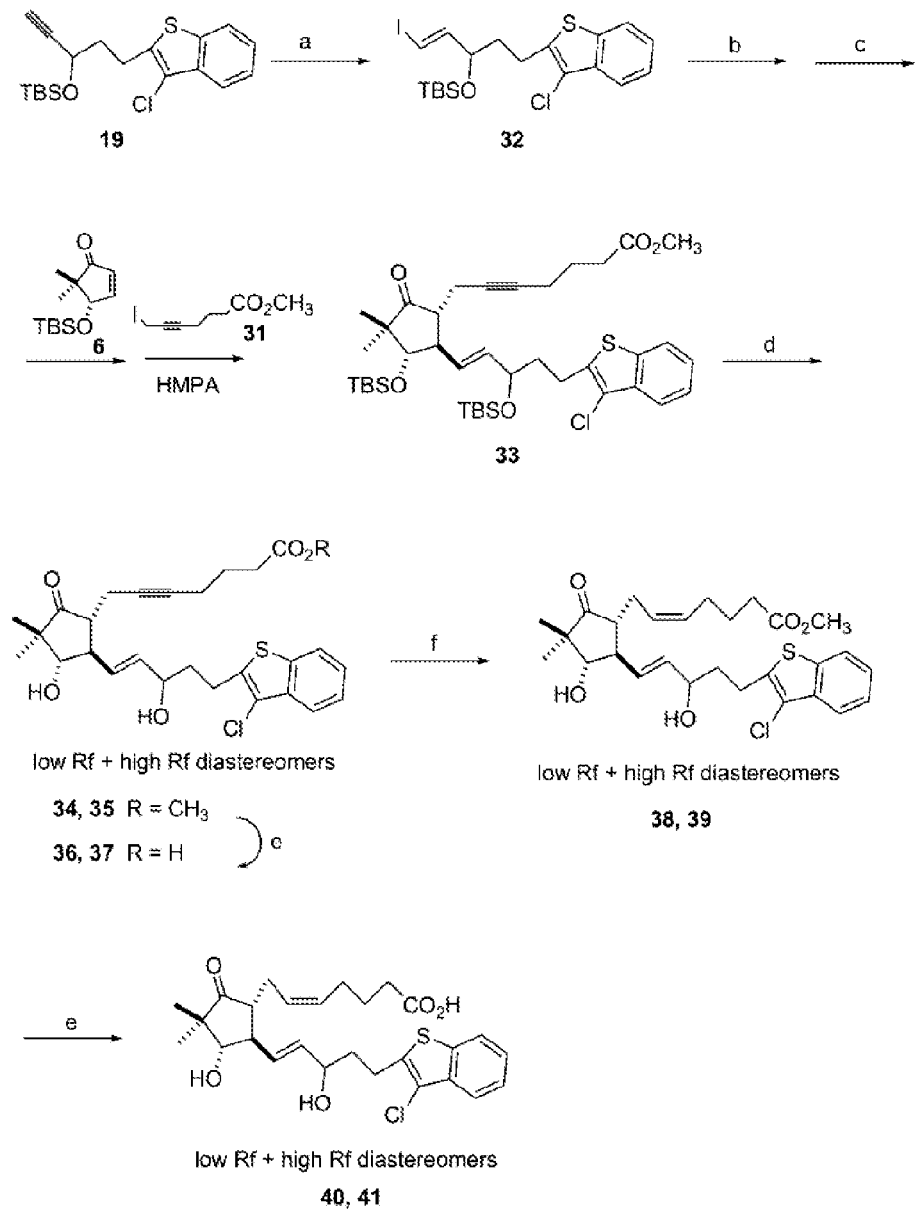

A solution of (30) (1.347 g, 8.6 mmol) in 5 mL dichloromethane was added to a mixture of triphenylphosphine (2.725 g, 10.4 mmol), imidazole (726 mg, 10.7 mmol), and iodine (2.602 g, 10.3 mmol) in 34 mL dichloromethane, rinsing with 5 mL dichloromethane. After 40 minutes, the dichloromethane was evaporated in vacuo to about 2 mL and the resulting mixture filtered through basic alumina, washing with 10% ethyl acetate/hexanes. Purification by flash chromatography on silica gel (10% ethyl acetate/hexanes) gave 1.878 g (7.1 mmol, 83%) of the propargyl iodide.

tert-Butyl-{[(E)-1-[2-(3-chloro-benzo[b]thiophen-2-yl)-ethyl]-3-iodo-allyloxy}-dimethyl-silane (32, FIG. 5)

A solution of alkyne (19) (5.547 g, 15.2 mmol) in dichloromethane (50 mL) was treated with Cp$_2$ZrHCl (5.794 g, 22.5 mmol). The reaction was stirred for 45 minutes and then N-iodosuccinimide (4.966 g, 22.1 mmol) was added. After 15 minutes, saturated sodium bicarbonate solution (200 mL) was added and the mixture extracted with dichloromethane (2×100 mL). The combined dichloromethane solution was dried (MgSO$_4$), filtered and evaporated. Purification by flash chromatography on silica gel (0-5% ethyl acetate/hexanes) gave 6.608 g (13.1 mmol, 86%) of the vinyl iodide (32).

7-{(1R,4S,5R)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentyl}-hept-5-ynoic acid methyl ester (33, FIG. 5)

A −78° C. solution of iodide (32) (675 mg, 1.34 mmol) in THF (2.0 mL) was treated with tert-butyllithium (1.73 mL, 2.94 mL, 1.7 M/pentane). The dark red mixture was stirred for 25 minutes and then dimethylzinc (0.80 mL, 1.6 mmol, 2 M/toluene) was added. The solution was stirred at 0° C. for 15 minutes and then recooled to −78° C. A solution of enone (6) (208 mg, 0.87 mmol) in THF (1.0 mL) was added over 2 hours by syringe pump, rinsing with 0.5 mL THF. After 30 minutes, HMPA (1.34 mL, distilled from $CaH_2$) was added followed by a solution of propargyl iodide (31) (1.286 g, 4.83 mmol) in THF (1.0 mL). The solution was stirred in a −40° C. bath overnight and then 20 mL saturated ammonium chloride solution and 10 mL water were added. The mixture was extracted with dichloromethane (20 mL) and ethyl acetate (2×20 mL). The combined organic extracts were dried ($MgSO_4$), filtered and evaporated. Purification by flash chromatography on silica gel (5-10% ethyl acetate/hexanes) gave 198 mg (0.27 mmol, 31%) of (33).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid methyl ester (34, 35, FIG. 5)

A solution of (33) (198 mg, 0.27 mmol) in $CH_3CN$ (6.5 mL) was treated with HF-pyridine (1.2 mL). The solution was stirred for 3 hours and saturated sodium bicarbonate solution (120 mL) was added. The mixture was extracted with dichloromethane (3×50 mL) and the combined dichloromethane solution dried ($Na_2SO_4$), filtered and evaporated. Purification by flash chromatography (50% ethyl acetate/hexane) followed by preparative TLC (55% ethyl acetate/hexane) gave 55 mg (0.11 mmol, 41%) of the less polar diastereomer (34) and 51 mg (0.10 mmol, 37%) of the more polar diastereomer (35).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (low $R_f$ diastereomer, 36, FIG. 5)

A solution of (34) (9 mg, 0.017 mmol) and rabbit liver esterase (1 mg) in pH 7.2 phosphate buffer (2 mL)/$CH_3CN$ (0.1 mL) was stirred for 17 hours. The mixture was then coevaporated with $CH_3CN$ to remove water and the residue purified by flash chromatography on silica gel (3-7% MeOH/$CH_2Cl_2$) to give 8 mg (0.016 mmol, 93%) of the acid (36).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (high $R_f$ diastereomer, 37, FIG. 5)

A solution of (35) (12 mg, 0.023 mmol) and rabbit liver esterase (1 mg) in pH 7.2 phosphate buffer (2 mL)/$CH_3CN$ (0.1 mL) was stirred for 17 hours. TLC showed the presence of starting material, so another 2 mg of the esterase was added. After stirring for another 24 hours, the reaction was complete. Work up and purification as above for (36) gave 8 mg (0.016 mmol, 69%) of the acid (37).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (low $R_f$ diastereomer, 38, FIG. 5)

Ethanol (95%, 2.5 mL) was added to $NiCl_2$ (50 mg, 0.39 mmol) and $NaBH_4$ (7 mg, 0.19 mmol). The resulting black mixture was stirred for 5 minutes and then ethylenediamine (41 μL, 0.61 mmol) was added. After 15 minutes, a solution of alkyne (34) (40 mg, 0.077 mmol) in 0.5 mL 95% ethanol was added, rinsing with 0.5 mL ethanol. The flask was purged with $H_2$ and allowed to stir under 1 atm $H_2$ for 22 hours. The mixture was then filtered through celite and purified by flash chromatography on silica gel (55% ethyl acetate/hexanes) to give 17 mg (0.032 mmol, 43%) of the alkene (38).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (high $R_f$ diastereomer 39, FIG. 5)

The same procedure as for (36) was followed to give 17 mg (0.032 mmol, 41%) of (39).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (low $R_f$ diastereomer, 40, FIG. 5)

The same procedure as above for (36) was used to give 9 mg (0.018 mmol, 85%) of acid (40). 300 MHz $^1$H NMR ($CDCl_3$, ppm) δ 7.73 (2H, d, J=8.4 Hz) 7.45-7.30 (2H, m) 5.8-5.6 (2H, m) 5.4-5.3 (2H, m) 4.3-4.1 (1H, m) 3.57 (1H, d, J=9.7 Hz) 3.1-2.9 (2H, m) 2.5-1.9 (10H, m) 1.7-1.6 (2H, m) 1.09 (3H, s) 0.89 (3H, s).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (high $R_f$ diastereomer, 41, FIG. 5)

The same procedure as above for the (36) was used to give 9 mg (0.018 mmol, 85%) of acid (41). 300 MHz $^1$H NMR ($CDCl_3$, ppm) δ 7.73 (2H, d, J=8.8 Hz) 7.45-7.30 (2H, m) 5.8-5.6 (2H, m) 5.45-5.30 (2H, m) 4.3-4.2 (1H, m) 3.61 (1H, d, J=9.7 Hz) 3.1-3.0 (2H, m) 2.5-1.9 (10H, m) 1.7-1.6 (2H, m) 1.10 (3H, s) 0.90 (3H, s).

Figure 6:
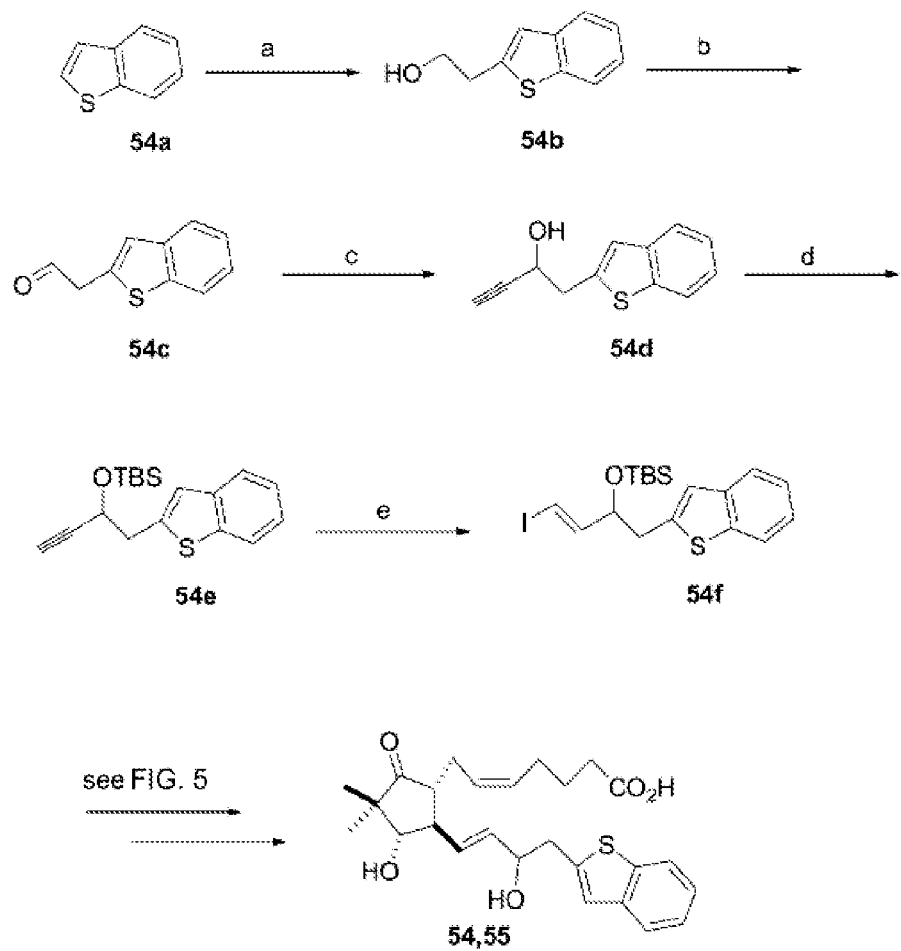

2-Benzo[b]thiophen-2-yl-ethanol (54b, FIG. 6)

n-BuLi (100 mL, 160 mmol, 1.6M/hexanes) was added to a −78° C. mixture of thianaphthene (54a) (17.31 g, 129 mmol) in THF (70 mL)/ether (30 mL). The mixture was stirred at −78° C. for 2 hours and then a solution of ethylene oxide (42.86 g, 1.071 mmol) in THF (70 mL)/ether (30 mL) was added by cannula over 15 minutes. The resulting mixture was stirred for 2 hours at −78° C. and then at room temperature for 15 hours. The mixture was evaporated, 200 mL water was added, and the resulting mixture was extracted with ethyl acetate (3×150 mL). The combined organic solution was washed with brine and then dried ($Na_2SO_4$), filtered, and evaporated. Purification by flash chromatography on silica gel (20% ethyl acetate/hexanes) gave (54b) (13.61 g, 78 mmol, 60%).

Benzo[b]thiophen-2-yl-acetaldehyde (54c, FIG. 6)

A 0° C. mixture of (54b) (8.019 g, 44.9 mmol) in 100 mL dichloromethane was treated with Dess-Martin reagent (20 g, 47.2 mmol). The mixture was stirred at 0° C. for 10 minutes and at room temperature for 40 minutes. Saturated $NaHCO_3$ solution (200 mL) and 0.1 M $NaHSO_3$ solution were added and the resulting mixture was extracted with ethyl acetate (3×300 mL). The combined organic solution was dried (Na$_2$SO$_4$), filtered and evaporated to give (54c) (8.77 g). The aldehyde was taken on crude for the next reaction.

1-Benzo[b]thiophen-2-yl-but-3-yn-2-ol (54d, FIG. 6)

A solution of crude (54c) (8.77 g) in THF (100 mL) was added to a solution of ethynylmagnesium bromide (450 mL, 225 mmol, 0.5 M/THF) at 0° C. by cannula. The mixture was stirred for 1 hour at 0° C. and for 1 hour at room temperature. The reaction was then quenched by addition of 200 mL saturated NH$_4$Cl solution. The layers were separated and the aqueous layer extracted with ethyl acetate (3×200 mL). The combined organic solution was washed with brine and then dried (Na$_2$SO$_4$), filtered and evaporated. Purification by flash chromatography on silica gel (10% 20% ethyl acetate/hexanes) gave (54d) (7.67 g, 37.9 mmol, 84% from 5-2).

(1-Benzo[b]thiophen-2-ylmethyl-prop-2-ynyloxy)-tert-butyl-dimethyl-silane (54e, FIG. 6)

DMAP (2.306 g, 18.9 mmol), TBSCl (11.502 g, 76.3 mmol) and triethylamine (5.25 mL, 37.7 mmol) were added to a solution of (54d) (7.67 g, 37.9 mmol) in dichloromethane (120 mL). After 17 hours, 150 mL of saturated NH$_4$Cl solution was added and the layers were separated. The aqueous layer was extracted with dichloromethane (3×100 mL) and the combined organic solution was dried (Na$_2$SO$_4$), filtered and evaporated. Purification by flash chromatography on silica gel (4% ethyl acetate/hexanes) gave (54e) (8.38 g, 26.5 mmol, 70%).

((E)-1-Benzo[b]thiophen-2-ylmethyl-3-iodo-allyloxy)-tert-butyl-dimethyl-silane (54f, FIG. 6)

Cp$_2$ZrHCl (1.719 g, 6.67 mmol) was added to a solution of (54e) (1.372 g, 4.34 mmol) in dichloromethane (30 mL). The reaction was stirred for 30 minutes at room temperature and N-iodosuccinimide (1.997 g, 8.88 mmol) was added. After 1 hour, the reaction was poured into 100 mL of saturated NaHCO$_3$ solution. The resulting mixture was extracted with dichloromethane (3×75 mL) and the combined organic extracts dried (Na$_2$SO$_4$), filtered and evaporated. Purification by flash chromatography on silica gel (2% ethyl acetate/hexanes) gave (54f) (1.7484 g, 91%).

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (54, 55, FIG. 6)

A solution of (54f) was treated in a manner similar to the scheme outlined in FIG. 5 to produce (54) and (55).

Figure 7:
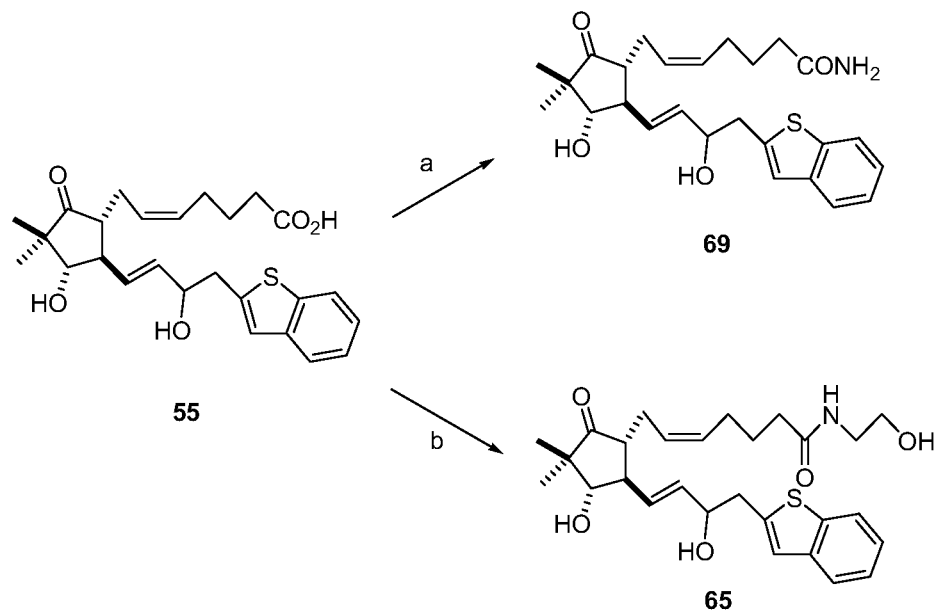

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (2-hydroxy-ethyl)-amide (60-63, 65, FIG. 7)

A solution of acid (55) (7 mg, 0.015 mmol) in DMF (0.5 mL) was treated with N-hydroxysuccinimide (6.9 mg, 0.056 mmol). The mixture was stirred for 5 minutes and 1-[3-(dimethylamino)propyl]-3-ethylcarbodiimide hydrochloride (EDCl, 20.7 mg, 0.11 mmol) was added. After stirring for 7 hours, 2-aminoethanol (5 µL, 0.083 mmol) was added and the mixture stirred further for 16 hours. Ethyl acetate (50 mL) was added and the mixture washed with water (3×50 mL) and brine (50 mL). The organic layer was dried (Na$_2$SO$_4$), filtered and evaporated. Purification by flash chromatography on silica gel (5% methanol/dichloromethane) followed by preparative thin layer chromatography (10% methanol/dichloromethane) gave amide (65) (5 mg, 0.010 mmol, 65%). Amides (60-63) were prepared in a similar manner.

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid amide (69, FIG. 7)

A solution of acid (55) (9 mg, 0.02 mmol) in dichloromethane (0.2 mL) was treated with triethylamine (15 µL, 0.11 mmol). The solution was cooled to 0° C. and after 10 minutes, ethyl chloroformate (7 µL, 0.073 mmol) was added. The solution was stirred further for 1 hour at 0° C. and then concentrated aqueous ammonium hydroxide solution was added (10 µL, 0.26 mmol). The reaction was stirred at room temperature overnight and then quenched by addition of 0.5 M HCl (7 mL). The mixture was extracted with ethyl acetate (3×30 mL), the combined ethyl acetate solution washed with saturated NaHCO$_3$ solution (20 mL) and brine (20 mL), and then dried (Na$_2$SO$_4$), filtered and evaporated. Purification by flash chromatography on silica gel (2%-6% methanol/dichloromethane) gave the title amide (2.6 mg, 28%).

Example 2

Compounds of Formula I Promote Synthesis of TGF-β and VEGF

This example illustrates that compounds of formula I promote formation of blood vessels.

To test whether the compounds of Formula I promote the formation of blood vessels, and incisional wound model was employed over a 14-day period. Sprague-Dawley rats (180-200 g) were anesthetized, the backs shaved, and a 2-cm long incision was made on the back skin of rats under sterile conditions, reaching the deep fascia. The wound was immediately closed with 4-0 sutures. The animals were topically treated with vehicle or Compound 1 at 0.004% twice daily. The vehicle contains ethanol 30%, propylene glycol 12%, dipropylene glycol 5%, benzyl alcohol 5%, glycerol 3% and normal saline 45%. Biopsy samples of skin wound tissues were analyzed with Western blots day-7 and day-14 post-surgery. Tissue samples about 1 mm thick were taken from both sides of the wound. Protein was extracted, and FGF-2/VEGF expression was monitored, with Western blot analysis.

Compound 1 treatment significantly enhanced the expression of FGF-2 by 60%, as normalized with β-actin (a housekeeping gene) by day-7 of the experiment (P=0.004). This significantly different increase in FGF-2 synthesis persisted for the whole study period (P=0.04). VEGF expression increased 25% as normalized with β-actin, by Compound 1 treatment on day-7 (P=0.039). This significantly different increase is synthesis returned to the baseline by day-14. Such an increase in FGF-2 and VEGF is consistent with their role in new blood vessel formation. The up-regulation of FGF-2 and VEGF by Compound 1 treatment was also observed in studies using an oral ulcer wound model.

Example 3

Adipose Tissue Transplant for Breast Defect Correction

This example illustrates the use of compositions and methods disclosed herein for a breast defect correction.

A 32-year-old woman presented with complaints that the medial portions of her breast implants were visible, which accentuated the "bony" appearance of her sternum. In addition she felt her breast were too far apart. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. The harvested area is injected subcutaneously with a standard tumescent fluid solution containing a saline solution, 0.5% lidocaine, and about 0.001% epinephrine. Using an 11-blade scalpel, a small puncture wound is made in order to transverse the dermis. The blade is turned 360 degrees to complete the wound. A two-holed blunt harvesting cannula (3 mm inner diameter) connected to a vacuum pump at low negative pressure (0.5 atm) is then inserted into the subcutaneous adipose tissue plane. The cannula is then moved throughout the plane to disrupt the connective tissue architecture. The volume of aspirate obtained is about 300 mL. The harvest adipose tissue is processed by centrifugation at 3,000 g for 3 minutes to separate health adipocytes and regenerative cells from blood, infiltration fluid and cell debris.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 3 mL syringes. One-holed blunt infiltration cannulas (3 mm inner diameter) are used to place the adipose tissue subcutaneously over the lateral sternum and medial breast bilaterally, 70 mL on the right and 50 mL on the left. The adipose tissue is administered in a tear like fashion to increase the surface area to volume ratio.

Alternatively, the adipose tissue is first administered into the individual, and a compound of formula I, such as, e.g., Compound 1, Compound 2, Compound 3, Compound 4, and/or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately one month after the procedure, the woman indicates that his quality of life has improved.

Example 4

Adipose Tissue Transplant for Breast Augmentation

This example illustrates the use of compositions and methods disclosed herein for a breast augmentation.

A 28-year-old woman presented micromastia or breast hypoplasia. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. Using a 10-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 600 mL. The harvest adipose tissue is processed by centrifugation at 2,700 g for 5 minutes to separate healthy adipocytes and regenerative cells from blood, infiltration fluid and cell debris. The centrifuged adipose tissue is then washed once is a Ringer's saline solution with lactone.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously using axillary, periareolar, and inframammary routes bilaterally, 190 mL on the right and 245 mL on the left. The adipose tissue is administered in a tear like fashion to increase the surface area to volume ratio.

Alternatively, the adipose tissue is first administered into the individual, and a compound of formula I, such as, e.g., Compound 1, Compound 2, Compound 3, Compound 4, and/ or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately one month after the procedure, the woman indicates that his quality of life has improved.

Example 5

Adipose Tissue Transplant for Breast Disorder

This example illustrates the use of compositions and methods disclosed herein for a breast disorder.

A 29-year-old woman presented with bilateral tuberous breast deformity. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdomen, buttock, lateral and medial thigh, and trochanter regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 1,400 mL.

The harvested adipose tissue is divided into two, approximately equal portions. One portion is processed by gravity sedimentation to separate health adipocytes and regenerative cells from blood, infiltration fluid and cell debris. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the sediment purified adipose tissue.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously in multiple planes axillary, periareolar, and inframammary routes bilaterally, 380 mL on the right and 370 mL on the left. The adipose tissue is administered in a tear like fashion to increase the surface area to volume ratio.

Alternatively, the adipose tissue is first administered into the individual, and a compound of formula I, such as, e.g., Compound 1, Compound 2, Compound 3, Compound 4, and/or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately one month after the procedure, the woman indicates that his quality of life has improved.

Example 6

Adipose Tissue Transplant for Facial Defects of Check

This example illustrates the use of compositions and methods disclosed herein for a facial disorder.

A 28-year-old woman presented with a lean face. She felt her face looked old, sad and bitter because of the less fullness of her cheek contour. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdominal region. The harvested area is injected subcutaneously with a standard tumescent fluid solution containing a saline solution, 0.08% lidocaine, and about 0.001% epinephrine. Using an 11-blade scalpel, a small puncture wound is made in order to transverse the dermis. The blade is turned 360 degrees to complete the wound. A two-holed blunt harvesting cannula (2.5 mm inner diameter) connected to a 60 mL syringe is then inserted into the subcutaneous adipose tissue plane. The cannula is then moved throughout the plane to disrupt the connective tissue architecture. The volume of aspirate obtained is about 50 mL. The harvest adipose tissue is processed by washing the harvested tissue with saline to remove lidocaine, oil and residual blood. The washed tissue is then centrifugation at 100 g for 2 minutes to separate health adipocytes and regenerative cells from any remaining blood, infiltration fluid and cell debris.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 20 mL syringes. One-holed blunt infiltration cannulas (3 mm inner diameter) are used to place about 15 mL of adipose tissue subcutaneously and under superficial musculoaponeurotic system into the left and right checks.

Alternatively, the adipose tissue is first administered into the individual, and a compound of formula I, such as, e.g., Compound 1, Compound 2, Compound 3, Compound 4, and/or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that his quality of life has improved.

Example 7

Adipose Tissue Transplant for Facial Defects of Eyelids

This example illustrates the use of compositions and methods disclosed herein for a facial disorder.

A 37-year-old woman presented with sunken eyes and this appearance made her look old and fierce. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To adipose tissue is harvested from the woman as described in Example 6.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 20 mL syringes. One-holed blunt infiltration cannulas (3 mm inner diameter) are used to place about 2.5 mL of adipose tissue subcutaneously and under superficial musculoaponeurotic system into the upper eyelid regions.

Alternatively, the adipose tissue is first administered into the individual, and a compound of formula I, such as, e.g., Compound 1, Compound 2, Compound 3, Compound 4, and/ or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 8

Adipose Tissue Transplant for Facial Defects

This example illustrates the use of compositions and methods disclosed herein for a breast disorder.

A 33-year-old woman presented with depressed bilateral temporal and cheek areas. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

The adipose tissue is harvested from the woman as described in Example 6, except that 200 mL of adipose tissue is collected.

The harvested adipose tissue is divided into two, approximately equal portions. One portion is processed by saline washing and centrifugation as described in Example 6. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the purified adipose tissue.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place about 16 mL of adipose tissue subcutaneously and under superficial musculoaponeurotic system into the left and right temporal and cheeks regions.

Alternatively, the adipose tissue is first administered into the individual, and a compound of formula I, such as, e.g., Compound 1, Compound 2, Compound 3, Compound 4, and/or Compound 5, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 9

Adipose Tissue Transplant to Treat Stress Urinary Incontinence

This example illustrates the use of compositions and methods disclosed herein for treating stress urinary incontinence.

A 55 year old man presents with urinary incontinence. Pre-operative evaluation of the patient includes routine history and physical examination in addition to thorough informed consent disclosing all relevant risks and benefits of the procedure. The physician evaluating the individual determines that he is a candidate for a soft tissue replacement method using the compositions and methods disclosed herein.

To begin the procedure, adipose tissue is harvested from the man. The procedure is performed at the individual's bedside. The physician examines the individual's habitus for a suitable site or sites to harvest adipose tissue and selects the abdomen, and lateral and medial thigh regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 900 mL.

A compound of formula I, such as, e.g., Compound 1, Compound 2, Compound 3, Compound 4, and/or Compound 5, is mixed with the processed adipose tissue. The amount of compound added is an amount sufficient to promote formation of a blood supply sufficient to support the transplanted tissue. This composition is then transferred to 20 mL syringes. One-holed blunt infiltration cannulas (14-gauge) are used to place about 800 mL of adipose tissue transdermally into the bladder neck and proximal urethra regions.

Alternatively, the adipose tissue is first administered into the individual, and a compound of formula I, such as, e.g., Compound 1, Compound 2, Compound 3, Compound 4, and/ or Compound 5, is subsequently administered into the same, or in the vicinity of, the region where the adipose tissue was implanted.

The individual is monitored after the procedure. Approximately three days after the transplant, the he experiences a decreased frequency of incontinence. Approximately one month after the procedure, the individual indicates that his quality of life has improved. The physician evaluates the engrafted tissue and determines that the long-term engraftment was successful.

Example 10

Adipose Tissue Transplant for Breast Defect Correction

This example illustrates the use of compositions and methods disclosed herein for a breast defect correction.

A 56-year-old woman presents with a surgically removed breast due to cancer. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, a breast mound is formed using a TRAM-flap procedure. In this procedure, a portion of abdomen tissue, including skin, adipose tissue, minor muscles and connective tissues, is taken from the patient's abdomen and transplanted onto the breast site. This tissue is then used to create a breast mound.

A compound of formula I, such as, e.g., Compound 1, Compound 2, Compound 3, Compound 4, and/or Compound 5, is then administered into the breast mound region. The amount of compound administered is an amount sufficient to promote formation of a blood supply sufficient to support the transplanted tissue.

The individual is monitored for approximately 7 days. The physician evaluates the engrafted tissue and determines that the engraftment was successful. Both the woman and her physician are satisfied with the results of the procedure. Approximately one month after the procedure, the woman indicates that her quality of life has improved. Subsequent surgery is performed to create a nipple and areola.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:
1. A composition useful for augmenting a breast of a patient, the composition comprising:
   a) adipose tissue; and
   b) a compound selected from one of

Compound 1

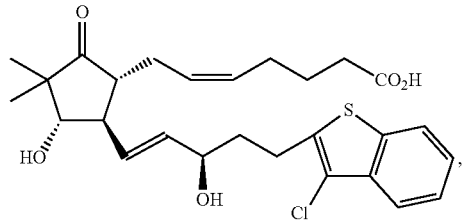

Compound 2

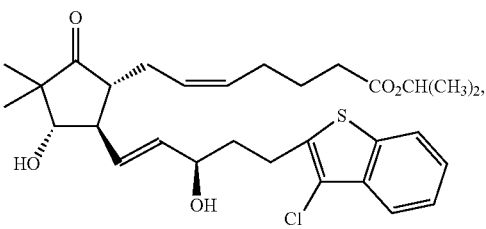

Compound 3

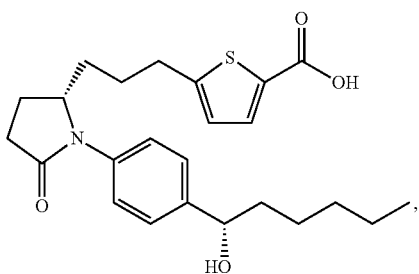

Compound 4

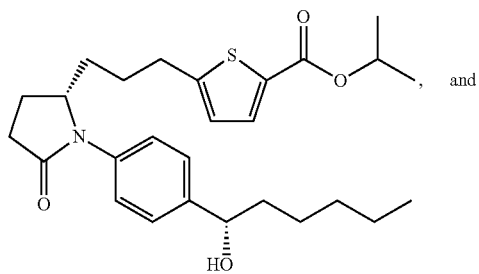

and

Compound 5

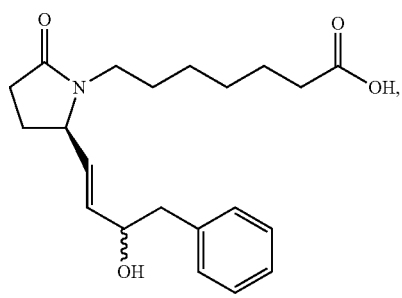

mixed with the adipose tissue;
the composition being effective, when introduced into a breast of a patient, for increasing breast size, and providing sustained engraftment of the adipose tissue in the breast.

2. The composition of claim 1 wherein the compound is Compound 1.
3. The composition of claim 1 wherein the compound is Compound 2.
4. The composition of claim 1 wherein the compound is Compound 3.
5. The composition of claim 1 wherein the compound is Compound 4.
6. The composition of claim 1 wherein the compound is Compound 5.
7. The composition of claim 1 wherein the adipose tissue is adipose tissue harvested from said patient.
8. The composition of claim 1 wherein the adipose tissue is adipose tissue harvested from an abdomen of said patient.

* * * * *